(12) United States Patent
Peters et al.

(10) Patent No.: US 7,060,699 B2
(45) Date of Patent: *Jun. 13, 2006

(54) ARYL AND HETEROARYL DIAZABICYCLOALKANES, THEIR PREPARATION AND USE

(75) Inventors: Dan Peters, Malmö (SE); Gunnar M Olsen, Frederiksberg (DK); Elsebet Østergaard Nielsen, Kobenhavn K (DK); Philip K. Ahring, Bagsvaerd (DK); Simon Feldbæk Nielsen, Herlev (DK); Tino Dyhring Jørgensen, Solrød Strand (DK)

(73) Assignee: Neurosearch A/S, Ballerup (DK)

( * ) Notice: Subject to any disclaimer, the term of this patent is extended or adjusted under 35 U.S.C. 154(b) by 334 days.

This patent is subject to a terminal disclaimer.

(21) Appl. No.: 10/276,160

(22) PCT Filed: Jun. 20, 2001

(86) PCT No.: PCT/DK01/00432

§ 371 (c)(1),
(2), (4) Date: Nov. 13, 2002

(87) PCT Pub. No.: WO02/02564

PCT Pub. Date: Jan. 10, 2002

(65) Prior Publication Data

US 2003/0176416 A1    Sep. 18, 2003

(30) Foreign Application Priority Data

Jul. 4, 2000   (DK) ............................. 2000 01037

(51) Int. Cl.
C07D 487/08    (2006.01)
C07D 471/08    (2006.01)
A61K 31/551    (2006.01)
A61K 31/395    (2006.01)
A61P 25/28     (2006.01)

(52) U.S. Cl. ................................ 514/221; 540/556
(58) Field of Classification Search ................ 540/556; 514/221
See application file for complete search history.

(56) References Cited

U.S. PATENT DOCUMENTS 6,552,012 B1 *  4/2003  Peters et al. ............... 514/183
2003/0225268 A1 * 12/2003 Bunnelle et al. ............ 540/581

FOREIGN PATENT DOCUMENTS

| WO | WO 97/40049 A1 | 10/1997 |
| WO | WO 98/54181 A1 | 12/1998 |
| WO | WO 98/54182 A1 | 12/1998 |
| WO | WO 00/44755 A1 | 8/2000 |
| WO | WO 00/66586 A1 | 11/2000 |

OTHER PUBLICATIONS

Jensen et al., Journal of Labelled Compounds and Radiopharmaceuticals, J Label Compd Radiopharm 2002, 45: pp. 181-189.

* cited by examiner

*Primary Examiner*—Bruck Kifle
(74) *Attorney, Agent, or Firm*—Birch, Stewart, Kolasch & Birch, LLP

(57) ABSTRACT

The present invention relates to novel aryl and heteroaryl diazabicycloalkane derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

10 Claims, No Drawings

ARYL AND HETEROARYL DIAZABICYCLOALKANES, THEIR PREPARATION AND USE

This application is the national phase under 35 U.S.C. § 371 of PCT International Application No. PCT/DK01/00432 which has an International filing date of Jun. 20, 2001, which designated the United States of America.

TECHNICAL FIELD

The present invention relates to novel aryl and heteroaryl diazabicycloalkane derivatives, which are found to be cholinergic ligands at the nicotinic, acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the monoamine receptors 5-HTR, DAR and NER, and the biogenic amine transporters for 5-HT, DA and NE.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel diazabicycloalkane derivatives represented by the general Formula I

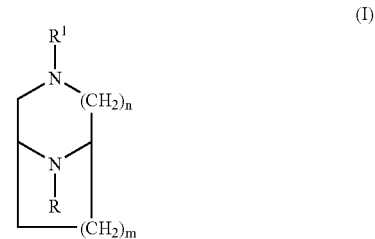

or a dimer thereof represented by any of Formulas II, III or IV

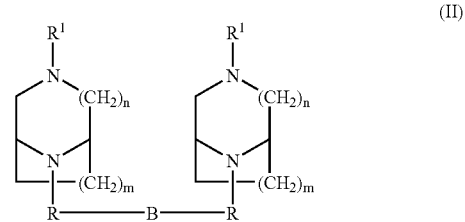

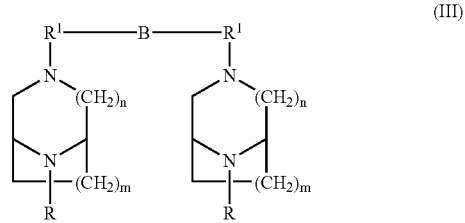

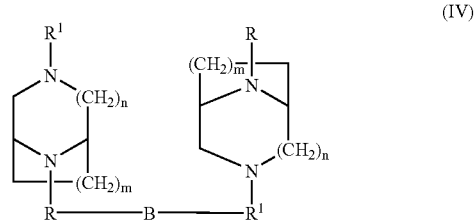

any of its enantiomers or any mixture thereof, an N oxide thereof, or a pharmaceutically acceptable salt thereof, in a labelled or un-labelled form, wherein, n is 2 or 3; and m is 1, 2 or 3; and one of R and $R^1$ represents hydrogen, alkyl, cycloalkyl, cycloalkylalkyl, alkenyl, alkynyl, a mono- or polycyclic aryl or aralkyl group; and the other of R and $R^1$ represents a mono- or polycyclic aryl group, which mono- or polycyclic aryl group may be substituted one or more times with alkyl, cycloalkyl, cycloalkylalkyl, alkoxy, hydroxyalkoxy, alkoxycycloalkyl, cycloalkoxy, cycloalkoxyalkoxy, alkenyl, alkenoxy, alkoxyalkenyl, alkynyl, alkynoxy, alkoxyalkynyl, alkylthio, alkenylthio, alkynylthio, alkylseleno, alkenylseleno, alkynylseleno, methylenedioxy, trifluoromethanesulfonyloxy, halogen, —OH, trihalogenmethyl, trihalogenmethoxy, —CN, amino, nitro, oxime, alkyloxime, acyloxime, or a group of the formula —COOR$^3$, —CONR$^2$R$^3$, —NH—CO$_2$R$^2$, —NHCO—R$^2$, —OCO—NR$^2$R$^3$; in which formulae R$^2$ and R$^3$ independently of each another represents hydrogen or alkyl; or which mono- or polycyclic aryl group may be substituted with a mono- or polycyclic aryl group, which aryl group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which mono- or polycyclic aryl group may be substituted with a group of the formula "—X-alkyl-Y-alkyl", wherein X and Y independently of each another represents O (epoxy), S, SO$_2$, NH, N-alkyl, NCO-alkyl, NSO$_2$-alkyl or Se, and the alkyl group is optionally substituted with alkoxy, or thioalkoxy; or which mono- or polycyclic aryl group may be substituted with a group of the formula "—X-(ALK)$_o$-aryl", or of the formula "—X-(ALK)$_o$-Y-aryl", wherein X and Y independently of each another represent O, S, SO$_2$, NH, N-alkyl, NCO-alkyl, NSO$_2$-alkyl or Se; "ALK" represents alkyl, alkenyl or alkynyl; o is 0 or 1; and aryl is a mono- or polycyclic aryl group which is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro oxime, alkyloxime, acyloxime; or which mono- or polycyclic aryl group may be substituted with a group of the formula "—X-(ALK)$_o$-HET", or of the formula "—X-(ALK)$_o$-Y-HET", wherein X and Y independently of each another represent O, S, SO$_2$, NH, N-alkyl, NCO-alkyl, NSO$_2$-alkyl or Se; "ALK" represents alkyl, alkenyl or alkynyl; o is 0 or 1; and "HET" represents a mono- or polycyclic heterocyclic aromatic group, which heterocyclic aromatic group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which mono- or polycyclic aryl group may be substituted with an monocyclic 5 to 6 membered heterocyclic group, which additional heterocyclic group is optionally substituted one or more times with alkyl, cycloalkyl, cycloalkylalkyl, alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which mono- or polycyclic aryl group may be substituted with a group of the formula "(ALK)$_o$-HET-", wherein "ALK" represents alkyl, alkenyl or alkynyl; o is 0 or 1; and "HET" represents a mono- or polycyclic heterocyclic aromatic group; or the other of R and R$^1$ represents a monocyclic 5 to 6 membered heterocyclic group, which monocyclic heterocyclic group may be substituted one or more times with alkyl, cycloalkyl, cycloalkylalkyl, alkoxy, hydroxyalkoxy, alkoxycycloalkyl, cycloalkoxy, cycloalkoxyalkoxy, alkenyl, alkenoxy, alkoxyalkenyl, alkynyl, alkynoxy, alkoxyalkynyl, alkylthio, alkenylthio, alkynylthio, alkylseleno, alkenylseleno, alkynylseleno, methylenedioxy, trifluoromethanesulfonyloxy, halogen, —OH, trihalogenmethyl, trihalogenmethoxy, —CN, amino, nitro, oxime, alkyloxime, acyloxime, or a group of the formula —COOR$^3$, —CONR$^2$R$^3$, —NH—O$_2$R$^2$, —NHCO—R$^2$, —OCO—NR$^2$R$^3$; in which formulas R$^2$ and R$^3$ independently of each another represents hydrogen or alkyl; or which monocyclic heterocyclic group may be substituted with a mono- or polycyclic aryl group, which aryl group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which monocyclic heterocyclic group may be substituted with a group of the formula "—X-alkyl-Y-alkyl", wherein X and Y independently of each another represents O (epoxy), S, SO$_2$, NH, N-alkyl, NCO-alkyl, NSO$_2$-alkyl or Se, and the alkyl group is optionally substituted with alkoxy, or thioalkoxy; or which monocyclic heterocyclic group may be substituted with a group of the formula "—X-(ALK)$_o$-aryl", or of the formula "—X-(ALK)$_o$-Y-aryl", wherein X and Y independently of each another represent O, S, SO$_2$, NH, N-alkyl, NCO-alkyl, NSO$_2$-alkyl or Se; "ALK" represents alkyl, alkenyl or alkynyl; o is 0 or 1; and aryl is a mono- or polycyclic aryl group which is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro oxime, alkyloxime, acyloxime; or which monocyclic heterocyclic group may be substituted with a group of the formula "—X-(ALK)$_o$-HET", or of the formula "—X-(ALK)$_o$-Y-HET", wherein X and Y independently of each another represent 9, S, SO$_2$, NH, N-alkyl, NCO-alkyl, NSO$_2$-alkyl or Se; "ALK" represents alkyl, alkenyl or alkynyl; o is 0 or 1; and "HET" represents a 5- or 6-membered monocyclic heterocyclic group, which heterocyclic group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which monocyclic heterocyclic group may be substituted with another monocyclic 5 to 6 membered heterocyclic group or with a polycyclic 5 to 6 membered heterocyclic group, which additional heterocyclic groups are optionally substituted one or more times with alkyl, cycloalkyl, cycloalkylalkyl, alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which monocyclic heterocyclic group may be substituted with a group of the formula "(ALK)$_o$-HET", wherein "ALK" represents alkyl, alkenyl or alkynyl; o is 0 or 1; and "HET" represents a monocyclic 5- to 6-membered heterocyclic group; or the other of R and R$^1$ represents a bicyclic or tricyclic heterocyclic group, composed of a 5 to 6 membered monocyclic heterocyclic group fused to a benzene ring or to another 5 to 6 membered heterocyclic group, which bi- or tricyclic heterocyclic group may be substituted one or more times with alkyl; cycloalkyl; cycloalkylalkyl; alkenyl; alkynyl; alkoxy; alkoxy-alkoxy; cycloalkoxy; alkenoxy; alkynoxy;

methylenedioxy; halogen; —OH; trihalogenmethyl, trihalogenmethoxy, —CN; amino; nitro; oxime; alkyloxime; or acyloxime;

a mono- or polycyclic aryl group, which aryl group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime;

a monocyclic 5- to 6-membered heterocyclic group, which heterocyclic group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; and optionally, R and/or $R^1$, together with the nitrogen atom to which they are attached, represent an alkyl-onium salt, a dialkyl-onium salt, a cycloalkyl-onium salt, an alkyl-cycloalkyl-onium salt, a dicycloalkyl-onium salt, an alkyl-cycloalkylalkyl-onium salt, a cycloalkyl-cycloalkylalkyl-onium salt, or a dicycloalkylalkyl-onium salt; and B represents a single bond bridge ("—", i.e. B is absent), or a bridging element of the formula "-ALK-", "-ALK-X-ALK-", "—X-ALK-X—", "-PHE-", "—X-PHE-X—", or "-ALK-PHE-ALK-"; wherein "ALK" represents a single bond bridge ("—", i.e. ALK is absent), or alkyl, alkenyl, or alkynyl; and "PHE" represents a phenylene (benzene-diyl) group; and X represents O, S, $SO_2$, NH, N-alkyl, NCO-alkyl, $NSO_2$-alkyl or Se; and "—R—B—R—" in Formula II represents a single bond bridge ("—", i.e. R and B are absent), or a bridging group of the formula "R—R—" (i.e. B is absent), or a bridging group of the formula "—R—" (i.e. R is absent in only one of the two compounds making up the dimeric substance); and "—$R^1$—B—$R^1$—" in Formula III represents a single bond bridge ("—", i.e. $R^1$ and B are absent), or a bridging group of the formula "$R^1$—$R^1$—" (i.e. B is absent), or a bridging group of the formula "—$R^1$—" (i.e. $R^1$ is absent in only one of the two compounds making up the dimeric substance); and "R—B—$R^1$" in Formula IV represents a single bond bridge ("—", i.e. R, B and $R^1$ are absent), or a bridging group of the formula "R—$R^1$—" (i.e. B is absent); or "R—B" in Formula IV represents a single bond bridge ("—", i.e. R and B are absent, $R^1$ is present); or "$R^1$—B" in Formula IV represents a single bond bridge ("—", i.e. $R^1$ and B are absent, R is present).

In another aspect the invention provides pharmaceutical compositions comprising a therapeutically effective amount of the diazabicycloalkane derivatives of the invention, or a pharmaceutically-acceptable addition salt thereof, together with at least one pharmaceutically-acceptable carrier or diluent, for the treatment, prevention or alleviation of a disease or a disorder or a condition that is responsive to modulation of cholinergic receptors and/or monoamine receptors.

In a third aspect the invention relates to the use of the diazabicycloalkane derivatives of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a fourth aspect the invention provides methods for treatment, prevention or alleviation of diseases, disorders or conditions of a living animal body, including a human, which disorders, diseases or conditions are responsive to modulation of cholinergic receptors and/or monoamine receptors, which method comprises the step of administering to such a living animal body in need thereof, a therapeutically effective amount of the diazabicycloalkane derivatives of the invention.

Other objects of the invention will be apparent to the person skilled in the art from the following detailed description and examples.

DETAILED DISCLOSURE OF THE INVENTION

Diazabicycloalkane Derivatives

In a first aspect novel diazabicycloalkane derivatives are provided. The diazabicycloalkane derivatives of the invention may be represented by the general Formula I

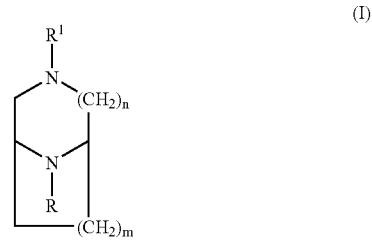

(I)

or it may be a dimeric compound represented by any of Formulas II, III or IV

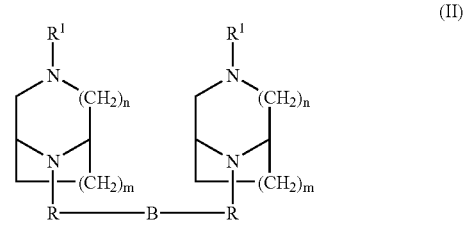

(II)

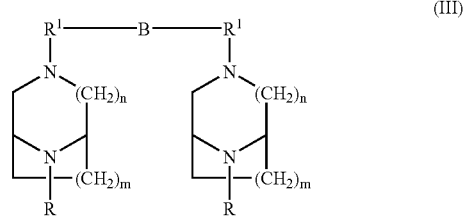

(III)

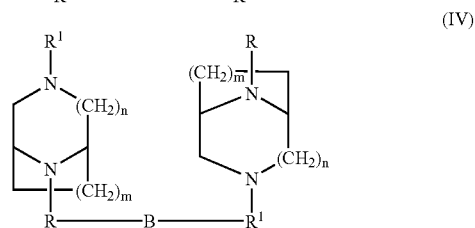

(IV)

an enantiomer or a mixture thereof, an N-oxide thereof, or a pharmaceutically acceptable salt thereof, and it may be in labelled or un-labelled form, wherein, n is 2 or 3; and m is 1, 2 or 3; and one of R and $R^1$ represents hydrogen, alkyl, cycloalkyl, cycloalkylalkyl, alkenyl, alkynyl, a mono- or polycyclic aryl or aralkyl group; and the other of R and $R^1$ represents a mono- or polycyclic aryl group, which mono- or polycyclic aryl group may be substituted one or more times with alkyl, cycloalkyl, cycloalkylalkyl, alkoxy, hydroxyalkoxy, alkoxycycloalkyl, cycloalkoxy, cycloalkoxyalkoxy, alkenyl, alkenoxy, alkoxyalkenyl, alkynyl, alkynoxy, alkoxyalkynyl, alkylthio, alkenylthio, alkynylthio, alkylseleno, alkenylseleno, alkynylseleno, methylenedioxy, trifluoromethanesulfonyloxy, halogen, —OH, trihalogenmethyl, trihalogenmethoxy, —CN, amino, nitro, oxime, alkyloxime, acyloxime, or a group of the formula —$COOR^3$, —$CONR^2R^3$, —NH—$CO_2R^2$, —NHCO—$R^2$, —OCO—$NR^2R^3$; in which formulae $R^2$ and $R^3$ independently of each another represents hydrogen or alkyl; or which mono- or polycyclic aryl group may be substituted with a mono- or polycyclic aryl group, which aryl group is optionally substituted one or more times with alkyl, cycloalkyl, cycloalkylalkyl-alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which mono- or polycyclic aryl group may be substituted with a group of the formula "—X-alkyl-Y-alkyl", wherein X and Y independently of each another represents O (epoxy), S, $SO_2$, NH, N-alkyl, NCO-alkyl, $NSO_2$-alkyl or Se, and the alkyl group is optionally substituted with alkoxy, or thioalkoxy; or which mono- or polycyclic aryl group may be substituted with a group of the formula "—X-$(ALK)_o$-aryl", or of the formula "—X-$(ALK)_o$-Y-aryl", wherein X and Y independently of each another represent O, S, $SO_2$, NH, N-alkyl, NCO-alkyl, $NSO_2$-alkyl or Se; "ALK" represents alkyl, alkenyl or alkynyl; o is 0 or 1; and aryl is a mono- or polycyclic aryl group which is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro oxime, alkyloxime, acyloxime; or which mono- or polycyclic aryl group may be substituted with a group of the formula "—X-$(ALK)_o$-HET", or of the formula "—X-$(ALK)_o$-Y-HET", wherein X and Y independently of each another represent O, S, $SO_2$, NH, N-alkyl, NCO-alkyl, $NSO_2$-alkyl or Se; "ALK" represents alkyl, alkenyl or alkynyl; o is 0 or 1; and 'HET' represents a mono- or polycyclic heterocyclic aromatic group, which heterocyclic aromatic group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which mono- or polycyclic aryl group may be substituted with an monocyclic 5 to 6 membered heterocyclic group, which additional heterocyclic group is optionally substituted one or more times with alkyl, cycloalkyl, cycloalkylalkyl, alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which mono- or polycyclic aryl group may be substituted with a group of the formula "$(ALK)_o$-HET", wherein "ALK" represents alkyl, alkenyl or alkynyl; o is 0 or 1; and "HET" represents a mono- or polycyclic heterocyclic aromatic group; or the other of R and $R^1$ represents a monocyclic 5 to 6 membered heterocyclic group, which monocyclic heterocyclic group may be substituted one or more times with alkyl, cycloalkyl, cycloalkylalkyl, alkoxy, hydroxyalkoxy, alkoxycycloalkyl, cycloalkoxy, cycloalkoxyalkoxy, alkenyl, alkenoxy, alkoxyalkenyl, alkynyl, alkynoxy, alkoxyalkynyl, alkylthio, alkenylthio, alkynylthio, alkylseleno, alkenylseleno, alkynylseleno, methylenedioxy, trifluoromethanesulfonyloxy, halogen, —OH, trihalogenmethyl, trihalogenmethoxy, —CN, amino, nitro, oxime, alkyloxime, acyloxime, or a group of the formula —$COOR^3$, —$CONR^2R^3$, —NH—$CO_2R^2$, —NHCO—$R^2$, —OC, —$NR^2R^3$; in which formulas $R^2$ and $R^3$ independently of each another represents hydrogen or alkyl; or which monocyclic heterocyclic group may be substituted with a mono- or polycyclic aryl group, which aryl group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which monocyclic heterocyclic group may be substituted with a group of the formula "—X-alkyl-Y-alkyl", wherein X and Y independently of each another represents O (epoxy), S, $SO_2$, NH, N-alkyl, NCO-alkyl, $NSO_2$-alkyl or Se, and the alkyl group is optionally substituted with alkoxy, or thioalkoxy; or which monocyclic heterocyclic group may be substituted with a group of the formula "—X-$(ALK)_o$-aryl", or of the formula "—X-$(ALK)_o$-Y-aryl", wherein X and Y independently of each another represent O, S, $SO_2$, NH, N-alkyl, NCO-alkyl, $NSO_2$-alkyl or Se; "ALK" represents alkyl, alkenyl or alkynyl; o is 0 or 1; and aryl is a mono- or polycyclic aryl group which is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro oxime, alkyloxime, acyloxime; or which monocyclic heterocyclic group may be substituted with a group of the formula "—X-$(ALK)_o$-HET", or of the formula "—X-$(ALK)_o$-Y-HET", wherein X and Y independently of each another represent O, S, $SO_2$, NH, N-alkyl, NCO-alkyl, $NSO_2$-alkyl or Se; "ALK" represents alkyl, alkenyl or alkynyl; o is 0 or 1; and "HET" represents a 5- or 6-membered monocyclic heterocyclic group, which heterocyclic group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which monocyclic heterocyclic group may be substituted with another monocyclic 5 to 6 membered heterocyclic group or with a polycyclic 5 to 6 membered heterocyclic group, which additional heterocyclic groups are optionally substituted one or more times with alkyl, cycloalkyl, cycloalkylalkyl, alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which monocyclic heterocyclic group may be substituted with a group of the formula "$(ALK)_o$-HET", wherein "ALK" represents alkyl, alkenyl or alkynyl; o is 0 or 1; and "HET" represents a monocyclic 5- to 6-membered heterocyclic group; or the other of R and $R^1$ represents a monocyclic 5 to 6 membered heterocyclic group, which monocyclic heterocyclic group may be substituted one or more times with alkyl, cycloalkyl, cycloalkylalkyl, alkoxy, hydroxyalkoxy, alkoxycycloalkyl, cycloalkoxy, cycloalkoxyalkoxy, alkenyl, alkenoxy, alkoxyalkenyl, alkynyl, alkynoxy, alkoxyalkynyl, alkylthio, alkenylthio, alkynylthio, alkylseleno, alkenylseleno, alkynylseleno, methylenedioxy, trifluoromethanesulfonyloxy, halogen, —OH, trihalogenmethyl, trihalogenmethoxy, —CN, amino, nitro, oxime, alkyloxime, acyloxime, or a group of the formula —$COOR^3$, —$CONR^2R^3$, —NH—$CO_2R^2$, —NHCO—$R^2$, —OCO—$NR^2R^3$; in which formulae $R^2$ and $R^3$ independently of each another represents hydrogen or alkyl; or which monocyclic heterocyclic group may be substituted with a mono- or polycyclic aryl group, which aryl group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which monocyclic heterocyclic group may be substituted with a group of the formula "—X-alkyl-Y-alkyl", wherein X and Y independently of each another represents O (epoxy), S, $SO_2$, NH, N-alkyl, NCO-alkyl, $NSO_2$-alkyl or Se, and the alkyl group is optionally substituted with alkoxy, or thioalkoxy; or which monocyclic heterocyclic group may be substituted with a group of the formula "—X-(ALK)$_o$-aryl", or of the formula "—X-(ALK)$_o$-Y-aryl", wherein X and Y independently of each another represent O, S, $SO_2$, NH, N-alkyl, NCO-alkyl, $NSO_2$-alkyl or Se; "ALK" represents alkyl, alkenyl or alkynyl; o is 0 or 1; and aryl is a mono- or polycyclic aryl group which is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro oxime, alkyloxime, acyloxime; or which monocyclic heterocyclic group may be substituted with a group of the formula "—X-(ALK)$_o$-HET", or of the formula "—X-(ALK)$_o$-Y-HET", wherein X and Y independently of each another represent O, S, $SO_2$, NH, N-alkyl, NCO-alkyl, $NSO_2$-alkyl or Se; "ALK" represents alkyl, alkenyl or alkynyl; o is 0 or 1; and "HET" represents a 5- or 6-membered monocyclic heterocyclic group, which heterocyclic group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which monocyclic heterocyclic group may be substituted with another monocyclic 5 to 6 membered heterocyclic group or with a polycyclic 5 to 6 membered heterocyclic group, which additional heterocyclic groups are optionally substituted one or more times with alkyl, cycloalkyl, cycloalkylalkyl, alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; or which monocyclic heterocyclic group may be substituted with a group of the formula "(ALK)$_o$-HET", wherein "ALK" represents alkyl, alkenyl or alkynyl; o is 0 or 1; and "HET" represents a monocyclic 5- to 6-membered heterocyclic group; or the other of R and $R^1$ represents a bicyclic or tricyclic heterocyclic group, composed of a 5 to 6 membered monocyclic heterocyclic group fused to a benzene ring or to another 5 to 6 membered heterocyclic group, which bi- or tricyclic heterocyclic group may be substituted one or more times with alkyl, cycloalkyl, cycloalkylalkyl, alkenyl, alkynyl, alkoxy, alkoxy-alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime;

a mono- or polycyclic aryl group, which aryl group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime;

a monocyclic 5- to 6-membered heterocyclic group, which heterocyclic group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime; and optionally, R and/or $R^1$, together with the nitrogen atom to which they are attached, represent an alkyl-onium salt, a dialkyl-onium salt, a cycloalkyl-onium salt, an alkyl-cycloalkyl-onium salt, a dicycloalkyl-onium salt, an alkyl-cycloalkylalkyl-onium salt, a cycloalkyl-cycloalkylalkyl-onium salt, or a dicycloalkylalkyl-onium salt; and B represents a single bond bridge ("—", i.e. B is absent), or a bridging element of the formula "-ALK-", "-ALK-X-ALK-", "—X-ALK-X—", "-PHE-", "—X-PHE-X—", or "-ALK-PHE-ALK-"; wherein "ALK" represents a single bond bridge ("—", i.e. ALK is absent), or alkyl, alkenyl, or alkynyl; and "PHE" represents a phenylene (benzene-diyl) group; and X represents O, S, $SO_2$, NH, N-alkyl, NCO-alkyl, $NSO_2$-alkyl or Se; and "—R—B—R—" in Formula II represents a single bond bridge ("—", i.e. R and B are absent), or a bridging group of the formula "R—R—" (i.e. B is absent), or a bridging group of the formula "—R—" (i.e. R is absent in only one of the two compounds making up the dimeric substance); and "—$R^1$—B—$R^1$—" in Formula III represents a single bond bridge ("—", i.e. $R^1$ and B are absent), or a bridging group of the formula "$R^1$—$R^1$—" (i.e. B is absent), or a bridging group of the formula "—$R^1$—" (i.e. $R^1$ is absent in only one of the two compounds making up the dimeric substance); and "R—B—$R^1$" in Formula IV represents a single bond bridge ("—", i.e. R, B and $R^1$ are absent), or a bridging group of the formula "R—$R^1$—" (i.e. B is absent); or "R—B" in Formula IV represents a single bond bridge ("—", i.e. R and B are absent, $R^1$ is present); or "$R^1$—B" in Formula IV represents a single bond bridge ("—", i.e. $R^1$ and B are absent, R is present).

In a preferred embodiment, the diazabicycloalkane derivative of the invention is a 3,9-diazabicyclo-[4.2.1]-nonane derivative, i.e. diazabicycloalkane derivative of any of Formulas I–IV, wherein n is 2 and m is 1, or a 3,10-diazabicyclo-[4,3,1]-decane derivative, i.e. diazabicycloalkane derivative of any of Formulas I–IV, wherein n is 2 and m is 2.

In another preferred embodiment, the diazabicycloalkane derivative of the invention is represented by any of Formulas I–IV, wherein one of R and $R^1$ represents hydrogen or alkyl, and the other of R and $R^1$ represents a mono- or polycyclic aryl group, which group may be substituted once or twice with halogen, alkyl, alkoxy, trihalogenmethyl, trihalogenmethoxy, amino, —NHCO-alkyl, nitro, phenyl or pyrrolidinyl.

In a more preferred embodiment, the diazabicycloalkane derivative of the invention is represented by any of Formulas I–IV, wherein one of R or $R^1$ represents hydrogen or methyl, and the other of R or $R^1$ represents a phenyl group or a naphthyl group, which aryl groups may be substituted once or twice with chloro, bromo, fluoro, methoxy, trifluoromethyl, trifluoromethoxy, amino, —NHCO-$CH_3$, nitro, phenyl or pyrrolidinyl.

In a most preferred embodiment, the diazabicycloalkane derivative of Formula I of the invention is (±) 3-(2-Naphthalyl)-9-methyl-3,9-diazabicyclo-[4.2.1]-nonane;

(±) 3-(3,4-Dichlorophenyl)-9-methyl-3,9-diazabicyclo-[4.2.1]-nonane;

(±) 3-(4-Fluorophenyl)-9-methyl-3,9-diazabicyclo-[4.2.1]-nonane;

(±) 3-(3-Fluorophenyl)-9-methyl-3,9-diazabicyclo-[4.2.1]-nonane;

(±) 3-(4-Trifluoromethoxyphenyl)-9-methyl-3,9-diazabicyclo-[4.2.1]-nonane;

(±) 3-(3-Trifluoromethoxyphenyl)-9-methyl-3,9-diazabicyclo-[4.2.1]-nonane;

(±) 3-(Phenyl)-9-methyl-3,9-diazabicyclo-[4.2.1]-nonane;

(±) 3-(3-Chlorophenyl)-9-methyl-3,9-diazabicyclo-[4.2.1]-nonane;

(±) 3-(3-Bromophenyl)-9-methyl-3,9-diazabicyclo-[4.2.1]-nonane (±) 3-(4-Biphenylyl)-9-methyl-3,9-diazabicyclo-[4.2.1]-nonane (±) 3-(3,4-Dichlorophenyl)-9-H-3,9-diazabicyclo-[4.2.1-]-nonane;

(±) 3-Phenyl-9-H-3,9-diazabicyclo-[4.2.1]-nonane;

(±) 3-(3-Chlorophenyl)-9-H-3,9-diazabicyclo-[4.2.1]-nonane;

(±) 3-(4-Biphenylyl)-9-H-3,9-diazabicyclo-[4.2.1]-nonane;

(±) 3-(4-Nitrophenyl)-9-methyl-3,9-diazabicyclo-[4.2.1]-nonane;

(±) 3-(4-Trifluoromethylphenyl)-9-methyl-3,9-diazabicyclo-[4.2.1]-nonane;

(±) 3-(4-Aminophenyl)-9-methyl-3,9-diazabicyclo-[4.2.1]-nonane;

(±) 3-(4-Acetylaminophenyl)-9-methyl-3,9-diazabicyclo-[4.2.1]-nonane; or (±) 3-[4-(N-Pyrrolidinylphenyl)]-9-methyl-3,9-diazabicyclo-[4.2.1]-nonane;

an enantiomer or a mixture hereof, an N-oxide hereof, or a pharmaceutically acceptable salt thereof, and in labelled or un-labelled form.

In another preferred embodiment the diazabicycloalkane derivative of the invention is represented by any of Formulas I–IV, wherein one of R and $R^1$ represents hydrogen or alkyl, and the other of R and $R^1$ represents a bi- or tricyclic 5- to 6-membered heterocyclic group, which heterocyclic group may be substituted with a group of the formula "—X-(ALK)$_o$-HET", or of the formula "—X-(ALK)$_o$-Y-HET", wherein X and Y independently of each another represent O or S, "ALK" represents alkyl, alkenyl or alkynyl; o is 1; and "HET" represents a 5- or 6-membered monocyclic heterocyclic group, which heterocyclic group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, trihalogenmethyl, trihalogenmethoxy, —CN, amino, nitro, oxime, alkyloxime, or acyloxime.

In a more preferred embodiment, the diazabicycloalkane derivative of Formula I is 3-[(5-Chloropyrid-3-yl)-5-oxyethoxypydd-3-yl]-9-Methyl-3,9-diazabicyclo-[4.2.1]-nonane;

or an enantiomer or a mixture hereof, an N-oxide hereof, or a pharmaceutically acceptable salt thereof, and in labelled or un-labelled form.

In yet another preferred embodiment, the diazabicycloalkane derivative of the invention is represented by any of Formulas I–IV, wherein one of R and $R^1$ represents hydrogen or alkyl, and the other of R and $R^1$ represents a monocyclic 5- to 6-membered heterocyclic group, which group may be substituted once or twice with halogen, alkyl, alkoxy, trihalogenmethyl, trihalogenmethoxy, phenyl, methylphenyl, methoxyphenyl, nitrophenyl, dimethylaminosulfonyl-phenyl, pyridyl, thienyl, benzothiophenyl, chloropydidyl, chloropyridyfoxyethoxy, toluylpyridyl, phenylthio, pyridylthio, phenylsulphonyl, pyridylsulphonyl, phenylamino, pyridylamino, phenylacetylamino, pyridylacetylamino, phenoxy or pyridyloxy.

In a more preferred embodiment, the diazabicycloalkane derivative of the invention is represented by any of Formulas I–IV, wherein one of R or $R^1$ represents hydrogen or methyl, and the other of R or $R^1$ represents a thienyl group, a pyridyl group, a pyridazinyl group, which heterocyclic groups may be substituted once or twice with chloro, bromo, fluoro, methoxy, trifluoromethyl, trifluoromethoxy, amino, —NHCO—$CH_3$, nitro, phenyl, 2-methylphenyl, 2-methoxyphenyl, 3-nitrophenyl, 4-dimethylaminosulfonyl-phenyl, 3-pyridyl, 3-thienyl, 2-benzothiophenyl, 6-chloropyridyl, 5-chloropyrid-3-yl-5-oxyethoxy, 2-toluylpyridyl, 6-phenylthio, 6-pyridylthio, 6-phenylsulphonyl, 6-pyridylsulphonyl, 6-phenylamino, 6-pyridylamino, 6-phenylacetylamino, 6-pyridylacetylamino, 6-phenoxy or 6-pyridyloxy.

In its most preferred embodiment, the diazabicycloalkane derivative of the invention is (±) 3-(5-Phenyl-2-thienyl)-9-methyl-3,9-diazabicyclo-[4.2.1]-nonane;

(±) 3-[(5-Chloropyrid-3-yl)-5-oxyethoxypyrid-3-yl]-9-Methyl-3,9-diazabicyclo-[4.2.1]-nonane;

(±) 3-(6-Phenyl-3-pyridazinyl)-9-methyl-3,9-diazabicyclo-[4.2.1]-nonane;

(±) 3-(6-Phenyl-3-pyridazinyl)-10-methyl-3,10-diazabicyclo-[4.3.1]-decane;

(±) 3-(6-Bromo-3-pyridyl)-10-methyl-3,10-diazabicyclo-[4.3.1]-decane;

(±) 3-(6-Bromo-3-pyridyl)-10-H-3,10-diazabicyclo-[4.3.1]-decane;

(±) 3-(3-Pyridyl)-10-H-3,10-diazabicyclo-[4.3.1]-decane;

(±) 3-(6-Phenyl-3-pyridyl)-10-H-3,10-diazabicyclo-[4.3.1]-decane;

(±) 3-(3-Pyridyl)-10-methyl-3,10-diazabicyclo-[4.3.1]-decane;

(±) 3-(3-pyridyl)-9-methyl-3,9-diazabicyclo-[4.2.1]-nonane;

(±) 3-(6-Chloro-3-pyridyl)-10-methyl-3,10-diazabicyclo-[4.3.1]-decane;

(±) 3-(2-Toluyl-3-pyridyl)-9-methyl-3,9-diazabicyclo-[4.2.1]-nonane;
(±) 3-(2-Methoxy-phenyl-3-pyridyl)-9-methyl-3,9-diazabicyclo-[4.2.1]-nonane;
(±) 3-(4-Dimethylaminosulfonyl-phenyl-3-pyridyl)-9-methyl-3,9-diazabicyclo-4.2.1]-nonane;
(±) 3-(2-Benzothiophenyl-3-pyridyl)-9-methyl-3,9-diazabicyclo-[4.2.1]-nonane;
(±) 3-(3-Thienyl-3-pyridyl)-9-methyl-3,9-diazabicyclo-[4.2.1]-nonane;
(±) 3-(3-Pyridyl-3-pyridyl)-9-methyl-3,9-diazabicyclo-[4.2.1]-nonane;
(±) 3-(3-Nitrophenyl-3-pyridyl)-9-methyl-3,9-diazabicyclo-[4.2.1]-nonane;
(±) 3-H-9-(6-Phenyl-3-pyridaziny)l-3,9-diazabicyclo-[4.2.1]-nonane;
(±) 3-Methyl-9-(6-Phenyl-3-pyridaziny)l-3,9-diazabicyclo-[4.2.1]-nonane;
(±) 3-(6-Phenylthio-3-pyridyl)-9-H-3,9-diazabicyclo-[4.2.1]-nonane;
(±) 3-(6-Phenylthio-3-pyridyl)-9-methyl-3,9-diazabicyclo-[4.2.1]-nonane;
(±) 3-(6-Phenylthio-3-pyridyl)-10-H-3,10-diazabicyclo-[4.3.1]-decane;
(±) 3-(6-Phenylthio-3-pyridyl)-10-methyl-3,10-diazabicyclo-[4.3.1]-decane;
(±) 3-(6-Pyrid-2-ylthio-3-pyridyl)-9-H-3,9-diazabicyclo-[4.2.1]-nonane;
(±) 3-(6-Pyrid-2-ylthio-3-pyridyl)-9-methyl-3,9-diazabicyclo-[4.2.1]-nonane;
(±) 3-(6-Pyrid-2-ylthio-3-pyridyl)-10-H-3,10-diazabicyclo-[4.3.1]-decane;
(±) 3-(6-Pyrid-2-ylthio-3-pyridyl)-10-methyl-3,10-diazabicyclo-[4.3.1]-decane;
(±) 3-(6-Pyrid-3-ylthio-3-pyridyl)-9-H-3,9-diazabicyclo-[4.2.1]-nonane;
(±) 3-(6-Pyrid-3-ylthio-3-pyridyl)-9-methyl-3,9-diazabicyclo-[4.2.1]-nonane;
(±) 3-(6-Pyrid-3-ylthio-3-pyridyl)-10-H-3,10-diazabicyclo-[4.3.1]-decane;
(±) 3-(6-Pyrid-3-ylthio-3-pyridyl)-10-methyl-3,10-diazabicycio-[4.3.1]-decane;
(±) 3-(6-Pyrid-4-ylthio-3-pyridyl)-9-H-3,9-diazabicyclo-[4.2.1]-nonane;
(±) 3-(6-Pyrid-4-ylthio-3-pyridyl)-9-methyl-3,9-diazabicyclo-[4.2.1]-nonane;
(±) 3-(6-Pyrid-4-ylthio-3-pyridyl)-10-H-3,10-diazabicyclo-[4.3.1]-decane;
(±) 3-(6-Pyrid-4-ylthio-3-pyridyl)-10-methyl-3,10-diazabicyclo-[4.3.1]-decane;
(±) 3-(6-Phenylsulfonyl-3-pyridyl)-9-H-3,9-diazabicyclo-[4.2.1]-nonane;
(±) 3-(6-Phenylsulfonyl-3-pyridyl)-9-methyl-3,9-diazabicyclo-[4.2.1]-nonane;
(±) 3-(6-Phenylsulfonyl-3-pyridyl)-10-H-3,10-diazabicyclo-[4.3.1]-decane;
(±) 3-(6-Phenylsulfonyl-3-pyridyl)-10-methyl-3,10-diazabicyclo-[4.3.1]-decane;
(±) 3-(6-Pyrid-2-ylsulfonyl-3-pyridyl)-9-H-3,9-diazabicyclo-[4.2.1]-nonane;
(±) 3-(6-Pyrid-2-ylsulfonyl-3-pyridyl)-9-methyl-3,9-diazabicyclo-[4.2.1]-nonane;
(±) 3-(6-Pyrid-2-ylsulfonyl-3-pyridyl)-10-H-3,10-diazabicyclo-[4.3.1]-decane;
(±) 3-(6-Pyrid-2-ylsulfonyl-3-pyridyl)-10-methyl-3,10-diazabicyclo-[4.3.1]-decane;
(±) 3-(6-Pyrid-3-ylsulfonyl-3-pyridyl)-9-H-3,9-diazabicyclo-[4.2.1]-nonane;
(±) 3-(6-Pyrid-3-ylsulfonyl-3-pyridyl)-9-methyl-3,9-diazabicyclo-[4.2.1]-nonane;
(±) 3-(6-Pyrid-3-ylsulfonyl-3-pyridyl)-10-H-3,10-diazabicyclo-[4.3.1]-decane;
(±) 3-(6-Pyrid-3-ylsulfonyl-3-pyridyl)-10-methyl-3,10-diazabicyclo-[4.3.1]-decane;
(±) 3-(6-Pyrid-4-ylthio-3-pyridyl)-9-H-3,9-diazabicyclo-[4.2.1]-nonane;
(±) 3-(6-Pyrid-4-ylthio-3-pyridyl)-9-methyl-3,9-diazabicyclo-[4.2.1]-nonane;
(±) 3-(6-Pyrid-4-ylthio-3-pyridyl)-10-H-3,10-diazabicyclo-[4.3.1]-decane;
(±) 3-(6-Pyrid-4-ylthio-3-pyridyl)-10-methyl-3,10-diazabicyclo-[4.3.1]-decane;
(±) 3-(6-Phenylamino-3-pyridyl)-9-H-3,9-diazabicyclo-[4.2.1]-nonane;
(±) 3-(6-Phenylamino-3-pyridyl)-9-methyl-3,9-diazabicyclo-[4.2.1]-nonane;
(±) 3-(6-Phenylamino-3-pyridyl)-10-H-3,10-diazabicyclo-[4.3.1]-decane;
(±) 3-(6-Phenylamino-3-pyridyl)-10-methyl-3,10-diazabicyclo-[4.3.1]-decane;
(±) 3-(6-Pyrid-2-ylamino-3-pyridyl)-9-H-3,9-diazabicyclo-[4.2.1]-nonane;
(±) 3-(6-Pyrid-2-ylamino-3-pyridyl)-9-methyl-3,9-diazabicyclo-[4.2.1]-nonane;
(±) 3-(6-Pyrid-2-ylamino-3-pyridyl)-10-H-3,10-diazabicyclo-[4.3.1]-decane;
(±) 3-(6-Pyrid-2-ylamino-3-pyridyl)-10-methyl-3,10-diazabicyclo-[4.3.1]-decane;
(±) 3-(6-Pyrid-3-ylamino-3-pyridyl)-9-H-3,9-diazabicyclo-[4.2.1]-nonane;
(±) 3-(6-Pyrid-3-ylamino-3-pyridyl)-9-methyl-3,9-diazabicyclo-[4.2.1]-nonane;
(±) 3-(6-Pyrid-3-ylamino-3-pyridyl)-10-H-3,10-diazabicyclo-[4.3.1]-decane;
(±) 3-(6-Pyrid-3-ylamino-3-pyridyl)-10-methyl-3,10-diazabicyclo-[4.3.1]-decane;
(±) 3-(6-Pyrid-4-ylamino-3-pyridyl)-9-H-3,9-diazabicyclo-[4.2.1]-nonane;
(±) 3-(6-Pyrid-4-ylamino-3-pyridyl)-9-methyl-3,9-diazabicyclo-[4.2.1]-nonane;
(±) 3-(6-Pyrid-4-ylamino-3-pyridyl)-10-H-3,10-diazabicyclo-[4.3.1]-decane;
(±) 3-(6-Pyrid-4-ylamino-3-pyridyl)-10-methyl-3,10-diazabicyclo-[4.3.1]-decane;
(±) 3-(6-Phenyl-acetylamino-3-pyridyl)-9-H-3,9-diazabicyclo-[4.2.1]-nonane;
(±) 3-(6-Phenyl-acetylamino-3-pyridyl)-9-methyl-3,9-diazabicyclo-[4.2.1]-nonane;
(±) 3-(6-Phenyl-acetylamino-3-pyridyl)-10-H-3,10-diazabicyclo-[4.3.1]-decane;
(±) 3-(6-Phenyl-acetylamino-3-pyridyl)-10-methyl-3,10-diazabicyclo-[4.3.1]-decane;
(±) 3-(6-Pyrid-2-yl-acetylamino-3-pyridyl)-9-H-3,9-diazabicyclo-[4.2.1]-nonane;
(±) 3-(6-Pyrid-2-yl-acetylamino-3-pyridyl)-9-methyl-3,9-diazabicyclo-[4.2.1]-nonane;
(±) 3-(6-Pyrid-2-yl-acetylamino-3-pyridyl)-10-H-3,10-diazabicyclo-[4.3.1]-decane;
(±) 3-(6-Pyrid-2-yl-acetylamino-3-pyridyl)-10-methyl-3,10-diazabicyclo-[4.3.1]-decane;
(±) 3-(6-Pyrid-3-yl-acetylamino-3-pyridyl)-9-H-3,9-diazabicyclo-[4.2.1]-nonane;

(±) 3-(6-Pyrid-3-yl-acetylamino-3-pyridyl)-9-methyl-3,9-diazabicyclo-[4.2.1]-nonane;
(±) 3-(6-Pyrid-3-yl-acetylamino-3-pyridyl)-10-H-3,10-diazabicyclo-[4.3.1]-decane;
(±) 3-(6-Pyrid-3-yl-acetylamino-3-pyridyl)-10-methyl-3,10-diazabicyclo-[4.3.1]-decane;
(±) 3-(6-Pyrid-4-yl-acetylamino-3-pyridyl)-9-H-3,9-diazabicyclo-[4.2.1]-nonane;
(±) 3-(6-Pyrid-4-yl-acetylamino-3-pyridyl)-9-methyl-3,9-diazabicyclo-[4.2.1]-nonane;
(±) 3-(6-Pyrid-4-yl-acetylamino-3-pyridyl)-10-H-3,10-diazabicyclo-[4.3.1]-decane;
(±) 3-(6-Pyrid-4-yl-acetylamino-3-pyridyl)-10-methyl-3,10-diazabicyclo-[4.3.1]-decane;
(±) 3-(6-Phenoxy-3-pyridyl)-9-H-3,9-diazabicyclo-[4.2.1]-nonane;
(±) 3-(6-Phenoxy-3-pyridyl)-9-methyl-3,9-diazabicyclo-[4.2.1]-nonane;
(±) 3-(6-Phenoxy-3-pyridyl)-10-H-3,10-diazabicyclo-[4.3.1]-decane;
(±) 3-(6-Phenoxy-3-pyridyl)-10-methyl-3,10-diazabicyclo-[4.3.1]-decane;
(±) 3-(6-Pyrid-2-yl-oxy-3-pyridyl)-9-H-3,9-diazabicyclo-[4.2.1]-nonane;
(±) 3-(6-Pyrid-2-yl-oxy-3-pyridyl)-9-methyl-3,9-diazabicyclo-[4.2.1]-nonane;
(±) 3-(6-Pyrid-2-yl-oxy-3-pyridyl)-10-H-3,10-diazabicyclo-[4.3.1]-decane;
(±) 3-(6-Pyrid-2-yl-oxy-3-pyridyl)-10-methyl-3,10-diazabicyclo-[4.3.1]-decane;
(±) 3-(6-Pyrid-3-yl-oxy-3-pyridyl)-9-H-3,9-diazabicyclo-[4.2.1]-nonane;
(±) 3-(6-Pyrid-3-yl-oxy-3-pyridyl)-9-methyl-3,9-diazabicyclo-[4.2.1]-nonane;
(d 3-(6-Pyrid-3-yl-oxy-3-pyridyl)-10-H-3,10-diazabicyclo-[4.3.1]-decane;
(±) 3-(6-Pyrid-3-yl-oxy-3-pyridyl)-10-methyl-3,10-diazabicyclo-[4.3.1]-decane;
(±) 3-(6-Pyrid-4-yl-oxy-3-pyridyl)-9-H-3,9-diazabicyclo-[4.2.1]-nonane;
(±) 3-(6-Pyrid-4-yl-oxy-3-pyridyl)-9-methyl-3,9-diazabicyclo-[4.2.1]-nonane;
(±) 3-(6-Pyrid-4-yl-oxy-3-pyridyl)-10-H-3,10-diazabicyclo-[4.3.1]decane; or
(±) 3-(6-Pyrid-4-yl-oxy-3-pyridyl)-10-methyl-3,10-diazabicyclo-[4.3.1]-decane;

any of its enantiomers or any mixture thereof, an N oxide thereof, or a pharmaceutically acceptable salt thereof, in a labelled or un-labelled form.

In still another preferred embodiment, the diazabicycloalkane derivative of the invention is represented by any of Formulas I–IV, wherein one of R and R¹ represents hydrogen or alkyl, and the other of R and R¹ represents a bi- or tricyclic 5- to 6-membered heterocyclic group, which heterocyclic group may be substituted once or twice with halogen, alkyl, alkoxy, trihalogenmethyl, trihalogenmethoxy, nitro or phenyl.

In a more preferred embodiment, the diazabicycloalkane derivative of the invention is represented by any of Formulas I–IV, wherein one of R and R¹ represents hydrogen or alkyl, and the other of R and R¹ represents a quinolinyl group, a naphtyridinyl group, an N-methyl-carbazolyl group, a dibenzothiophenyl group, or a dibenzofuryl group, which heterocyclic groups may be substituted once or twice with halogen, alkyl, alkoxy, trihalogenmethyl, trihalogenmethoxy, nitro or phenyl.

In a most preferred embodiment, the diazabicycloalkane derivative of the invention is (±) 3-(2-Quinolinyl)-9-methyl-3,9-diazabicyclo-[4.2.1]-nonane;
(±) 3-(6-Quinolinyl)-9-methyl-3,9-diazabicyclo-[4.2.1]-nonane;
(±) 3-(3-Quinolinyl)-9-methyl-3,9-diazabicyclo-[4.2.1]-nonane;
(±) 3-(3-Quinolinyl)-9-H-3,9-diazabicyclo-[4.2.1]-nonane;
(±) 3-(4-Methyl-2-quinolinyl)-9-methyl-3,9-diazabicyclo-[4.2.1]-nonane;
(±) 3-(6-Nitro-2-quinolinyl)-9-methyl-3,9-diazabicyclo-[4.2.1]-nonane;
(±) 3-(6-Nitro-2-quinolinyl)-9-H-3,9-diazabicyclo-4.2.1-nonane;
(±) 3-[2-(1,8-Naphtyridinyl)]-9-H-3,9-diazabicyclo-[4.2.1]-nonane;
(±) 3-[2-(1,8-Naphtyridinyl)]-9-methyl-3,9-diazabicyclo-[4.2.1]-nonane;
(±) 3-[2-(1,8-Naphtyridinyl)]-10-H-3,10-diazabicyclo-[4.3.1]-decane;
(±) 3-[2-(1,8-Naphtyridinyl)]-10-methyl-3,10-diazabicyclo-[4.3.1]-decane;
(±) 3-[2-(1,5-Naphtyridinyl)]-9-H-3,9-diazabicyclo-[4.2.1]-nonane;
(±) 3-[2-(1,5-Naphtyridinyl)]-9-methyl-3,9-diazabicyclo-[4.2.1]-nonane;
(±) 3-[2-(1,5-Naphtyridinyl)]-10-H-3,10-diazabicyclo-[4.3.1]-decane;
(±) 3-[2-(1,5-Naphtyridinyl)]-10-methyl-3,10-diazabicyclo-[4.3.1]-decane;
(±) 3-[2-(N-Methyl-carbazolyl)]-9-H-3,9-diazabicyclo-[4.2.1]-nonane;
(±) 3-[2-(N-Methyl-carbazolyl)]-9-methyl-3,9-diazabicyclo-[4.2.1]-nonane;
(±) 3-[2-(N-Methyl-carbazolyl)]-10-H-3,10-diazabicyclo-[4.3.1]-decane;
(±) 3-[2-(N-Methyl-carbazolyl)]-10-methyl-3,10-diazabicyclo-[4.3.1]-decane;
(±) 3-(2-Dibenzothiophenyl)-9-H-3,9-diazabicyclo-[4.2.1]-nonane;
(±) 3-(2-Dibenzothiophenyl)-9-methyl-3,9-diazabicyclo-[4.2.1]-nonane;
(±) 3-(2-Dibenzothiophenyl)-10-H-3,10-diazabicyclo-[4.3.1]-decane;
(±) 3-(2-Dibenzothiophenyl)-10-methyl-3,10-diazabicyclo-[4.3.1]-decane;
(±) 3-(2-Dibenzofuryl)-9-H-3,9-diazabicyclo-[4.2.1]-nonane;
(±) 3-(2-Dibenzofuryl)-9-methyl-3,9-diazabicyclo-[4.2.1]-nonane;
(±) 3-(2-Dibenzofuryl)-10-H-3,10-diazabicyclo-[4.3.1]-decane; or
(±) 3-(2-Dibenzofuryl)-10-methyl-3,10-diazabicyclo-[4.3.1]-decane;

any of its enantiomers or any mixture thereof, an N oxide thereof, or a pharmaceutically acceptable salt thereof, in a labelled or un-labelled form.

In still another preferred embodiment, the diazabicycloalkane derivative of the invention is represented by any of Formulas II–IV, wherein B represents a single bond, or a group of the formula "—X-ALK-X—", wherein "ALK" represents alkyl, alkenyl, or alkynyl; and X represents O, S, SO$_2$, NH, N-alkyl, NCO-alkyl, NSO$_2$-alkyl or Se.

In a more preferred embodiment, diazabicycloalkane of the invention is a compound of Formula II or Formula III, which is O,O'-bis-[5-(9-Methyl-3,9-diazabicyclo-[4.2.1]-nonan-3-yl)-3-pyridyl]-ethyleneglycol; or 5,5-Bis-3-(9-methyl-3,9-diazabicyclo-[4.2.1]-nonanyl)-2,2-bipyridyl;

any of its enantiomers or any mixture thereof, an N oxide thereof, or a pharmaceutically acceptable salt thereof, in a labelled or un-labelled form.

Definition of Substituents

In the context of this invention halogen represents fluorine, chlorine, bromine or iodine. Thus, a trihalogenmethyl group represents e.g. a trifluoromethyl group and a trichloromethyl group.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butdienyl; 1-, 2-, 3-, 4- or 5-hexenyl, or 1,3-hexdienyl, or 1,3,5-hextrienyl; 1-, 2-, 3-, 4-, 5-, 6-, or 7-octenyl, or 1,3-octdienyl, or 1,3,5-octtrienyl, or 1,3,5,7-octtetraenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-henynyl, or 1,3-hexdiynyl or 1,3,5-hextriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5-octtriynyl, or 1,3,5,7-octtetraynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, an alkenoxy group designates an "alkenyl-O—" group, an alkynoxy group designates an "alkynyl-O—" group, wherein alkyl, alkenyl and alkynyl are as defined above.

In the context of this invention an alkoxy-alkyl group designates an "alkyl-O-alkyl-" group, an alkoxy-alkenyl group designates an "alkyl-O-alkenyl-" group, and an alkoxy-alkynyl group designates an "alkyl-O-alkynyl-" group, wherein alkyl, alkenyl and alkynyl are as defined above.

In the context of this invention an alkoxy-alkoxy group designates an "alkyl-O-alkyl-O—" group, wherein alkyl is as defined above.

In the context of this invention a cycloalkoxy group designates a "cycloalkyl-O—" group, wherein cycloalkyl is as defined above.

In the context of this invention a cycloalkoxyalkoxy group designates a "cycloalkoxy-alkoxy-" group, and an alkoxycycloalkyl group designates an "alkoxy-cycloalkyl-" group, wherein cycloalkoxy and alkoxy are as defined above.

In the context of this invention an alkylthio group designates an "alkyl-S—" group (thioalkoxy), an alkenylthio group designates an "alkenyl-S—" group (thioalkenoxy), and an alkynylthio group designates an "alkynyl-S—" group (thioalkenoxy), wherein alkyl, alkenyl and alkynyl are as defined above. Likewise alkylthio-alkoxy, alkoxy-alkylthio, and alkylthio-alkylthio designate an alkylthio group as defined above, attached to another alkylthio group, or to an alkoxy group as defined above.

In the context of this invention an alkylseneno designates an "alkyl-Se—" group, an alkenylseneno designates an "alkenyl-Se—" group, an alkynylseneno designates an "alkynyl-Se—" group, wherein alkyl, alkenyl and alkynyl are as defined above.

In the context of this invention an amino group may be a primary (—NH$_2$), secondary (—NH-alkyl), or tertiary (—N(alkyl)$_2$) amino group, i.e. it may be substituted once or twice with an alkyl group as defined above.

In the context of this invention an acyl group designates a carboxy group (HOOC—), an alkyl-carbonyl group (alkyl-CO—), or a cycloalkyl-carbonyl (cycloalkyl-CO —), wherein alkyl and cycloalkyl are as defined above. Examples of preferred acyl groups of the invention include carboxy, acetyl, and propionyl.

In the context of this invention a mono- or polycyclic aryl group designates a monocyclic or polycyclic aromatic hydrocarbon group. Examples of preferred aryl groups of the invention include phenyl, naphthyl, indenyl, azulenyl, anthracenyl, and fluorenyl.

In the context of this invention an aralkyl group designates a mono- or polycyclic aryl group as defined above, which aryl group is attached to an alkyl group as also defined above. Examples of preferred aralkyl groups of the invention include benzyl, and phenethyl.

In the context of this invention a mono- or polycyclic heterocyclic group is a mono- or polycyclic group, which group holds one or more heteroatoms in its ring structure. Preferred heteroatoms include nitrogen (N), oxygen (O), and sulphur (S). One or more of the ring structures may in particular be aromatic (i.e. a heteroaryl), saturated or partially saturated. Preferred heterocyclic monocyclic groups of the invention include 5- and 6 membered heterocyclic monocyclic groups. Preferred poly-heterocyclic groups of the invention are the bi- and tricyclic heterocyclic groups.

Examples of preferred aromatic heterocyclic 5-membered monocyclic groups of the invention include
furan, in particular 2- or 3-furanyl;
thiophene, in particular 2- or 3-thienyl;
pyrrole (azole), in particular 1-, 2- or 3-pyrrolyl;
oxazole, in particular oxazol-(2-,4- or 5-)yl;
thiazole, in particular thiazol-(2-,4-, or 5-)yl;
imidazole, in particular imidazol-(1-,2-,4- or 5-)yl;
pyrazole, in particular pyrazol-(1-,3-,4- or 5-)yl;
isoxazole, in particular isoxazol-(3-,4- or 5-)yl;
isothiazole, in particular isothiazol-(3-,4- or 5-)yl;
1,2,3-oxadiazole, in particular 1,2,3-oxadiazol-(4- or 5-)yl;
1,2,4-oxadiazole, in particular 1,2,4-oxadiazol-(3- or 5-)yl;
1,2,5-oxadiazole, in particular 1,2,5-oxadiazol-(3- or 4-)yl;
1,2,3-triazole, in particular 1,2,3-triazol-(1-,4- or 5-)yl;
1,2,4-thiadiazole, in particular 1,2,4-thiadiazol-(3- or 5-)yl;
1,2,5-thiadiazole, in particular 1,2,5-thiadiazol-(3- or 4-)yl; and
1,3,4-thiadiazole, in particular 1,3,4-thiadiazol-(2- or 5-)yl.

Examples of preferred saturated or partially saturated heterocyclic monocyclic 5-membered groups of the invention include
1,3-dioxolan, in particular 1,3-dioxolan-(2- or 4-)yl;
imidazolidine, in particular imidazolidin-(1-,2-,3-,4- or 5-)yl;
2-imidazoline, in particular 2-imidazolin-(1-,2-,4- or 5-)yl;
3-imidazoline, in particular 3-imidazolin-(1-,2-,4- or 5-)yl;
4-imidazoline, in particular 4-imidazolin-(1-,2-,4- or 5-)yl;
2H-oxazole (oxazoline), in particular 2H-oxazol-(2-,4- or 5-)yl;
4H-oxazole (oxazolidine), in particular 4H-oxazol-(2-,4- or 5-)yl;
1,2,3-oxadiazoline, in particular 1,2,3-oxadiazol-(4- or 5-)yl;
1,2,4-oxadiazoline, in particular 1,2,4-oxadiazol-(3- or 5-)yl;
1,2,5-oxadiazoline, in particular 1,2,5-oxadiazol-(3- or 4-)yl;
1,2,3-oxadiazolidine, in particular 1,2,3-oxadiazol-(4- or 5-)yl;
1,2,4-oxadiazolidine, in particular 1,2,4-oxadiazol-(3- or 5-)yl;
1,2,5-oxadiazolidine, in particular 1,2,5-oxadiazol-(3- or 4-)yl;
2H-pyrrole (pyrroline), in particular 2H-pyrrol-(1-,2- or 3-)yl;
4H-pyrrole (pyrrolidine), in particular 4H-pyrrol-(1-,2- or 3-)yl;
pyrazolidine, in particular pyrazolidin-(1-,2-,3-,4- or 5-)yl;
2-pyrazoline, in particular 2-pyrazolin-(1-,3-,4- or 5-)yl; and
3-pyrazoline, in particular 3-pyrazolin-(1-,3-,4- or 5-)yl.

Examples of preferred aromatic heterocyclic 6-membered monocyclic groups of the invention include
pyridine, in particular pyridin-(2-,3- or 4-)yl;
pyridazine, in particular pyridazin-(3- or 4-)yl;
pyrimidine, in particular pyrimidin-(2-,4- or 5-)yl;
pyrazine, in particular pyrazin-(2-,3-,5- or 6-)yl;
1,3,5-triazine, in particular 1,3,5-triazin-(2-,4- or 6-)yl; and
phosphinine, in particular phosphinin-(2-,3- or 4-)yl.

Examples of preferred saturated or partially saturated heterocyclic monocyclic 6-membered groups of the invention include
1,4-dioxolane, in particular 1,4-dioxolan-(2- or 3-)yl;
1,4-dithiane, in particular 1,4-dithian-(2- or 3-)yl;
morpholine, in particular morpholin-(2-,3- or 4-)yl;
1,4-oxazine, in particular 1,4-oxazin-(2-)yl;
oxadiazine, in particular oxadiazin-(2-,3- or 5-)yl;
piperidine, in particular piperidin-(1-,2-,3- or 4-)yl;
piperazine, in particular piperazin-(1-,2-,3- or 4-)yl;
2H-pyrane, in particular 2H-pyran-(2-,3- or 4-)yl;
4H-pyrane, in particular 4H-pyran-(2-,3- or 4-)yl;
thiomorpholine, in particular thiomorpholin-(2-,3- or 4-)yl; and
1,3,5-trithiane, in particular 1,3,5-trithian-(2-)yl.

Examples of preferred aromatic heterocyclic bi-cyclic groups of the invention include
indolizine, in particular indolizin-(1-,2-,3-,5-,6-,7- or 8)yl;
indole, in particular indol-(1-,2-,3-,4-,5-,6- or 7)yl;
isoindole, in particular isoindol-(1-,2-,3-,4-,5-,6- or 7-)yl;
benzo[b]furan (benzofuran), in particular benzo[b]furan-(2-, 3-,4-,5-,6- or 7-)yl;
benzo[c]furan (isobenzofuran), in particular benzo[c]furan-(1-,3-,4-,5-,6- or 7-)yl;
benzo[b]thiophene (benzothiophene), in particular benzo[b]thiophen-(2-, 3-,4-,5-,6- or 7-)yl;
benzo[c]thiophene (isobenzothiophene), in particular benzo[c]thiophen-(1-,3-,4-,5-,6- or 7-)yl;
benzimidazole, in particular benzimidazol-(1-,2-,4-,5-,6- or 7-)yl;
benzthiazole, in particular benzthiazol-(2-,4-,5-,6- or 7-)yl;
purine, in particular purin-(2-,6- or 8-)yl;
quinoline, in particular quinolin-(2-,3-,4-,5-,6-,7- or 8-)yl;
isoquinoline, in particular isoquinolin-(1-,3-,4-,5-,6-,7- or 8-)yl;
cinnoline, in particular cinnolin-(3-,4-,5-,6-,7- or 8-)yl;
phthlazine, in particular phthlazin-(1-,4-,5-,6-,7- or 8-)yl;
quinazoline, in particular quinazolin-(2-,4-,5-,6-,7- or 8-)yl;
quinoxaline, in particular quinoxalin-(2-,3-,5-,6-,7- or 8-)yl;
1,8-naphthyridine, in particular 1,8-naphthyridin-(2-,3-,4-, 5-,6- or 7-)yl; and
pteridine, in particular pteridin-(2-,4-,6- or 7-)yl.

Examples of preferred saturated or partially saturated heterocyclic bi-cyclic groups of the invention include
indoline, in particular indolin-(1-,2-,3-,4-,5-,6- or 7-)yl;
3H-indole, in particular 3H-indol-(2-,3-,4-,5-,6- or 7-)yl;
1H-indazole, in particular 1H-indazol-(3-,4-,5-,6- or 7-)yl;
4H-quinolizine, in particular 4H-ouinolizin-(1-,2-,3-,4–6-, 7-,8- or 9-)yl;
quinuclidine, in particular quinuclidin-(2-,3-,4-,5-,6-,7- or 8-)yl;
isoquinuclidine, in particular isoquinuclidin-(1-,2-,3-,4-,5-, 6-,7- or 8-)yl;
tropane, in particular tropan-(1-,2-,3-,4-,5-,6-,7- or 8-)yl; and
nortropane, in particular nortropan-(1-,2-,3-,4-,5-,6- or 7-)yl.

Examples of preferred heterocyclic tricyclic groups of the invention include
naphtyridinyl, in particular 1,8-naphtyridinyl;
N-Methyl-carbazolyl;
dibenzothiophenyl, in particular 2-dibenzothiophenyl; and
dibenzofuryl, in particular 2-dibenzofuryl.

Pharmaceutically Acceptable Salts

The diazabicycloalkane derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Diazabicycloalkane Derivatives

The diazabicycloalkane derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention relates to novel aryl and heteroaryl diazabicycloalkane derivatives, which are found to be cholinergic ligands at the nicotinic acetylcholine receptors (nAChR), and modulators of the monoamine receptors, in particular the biogenic amine transporters 5-HT, DA and NE. Also preferred diazabicycloalkane derivatives of the invention show selective α7 activity.

In the context of this invention the term "modulator" covers agonists, partial agonists, antagonists and allosteric modulators of the receptor.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context 'treatment' covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Neuroimaging

The diazabicycloalkane derivatives of the invention may be useful as diagnostic tools or monitoring agents in various diagnostic methods, and in particular for in vivo receptor imaging (neuroimaging).

In another aspect of the invention, a method for the non-invasive determination of the distribution of a tracer compound inside a whole, intact living animal or human body using a physical detection method is provided. According to this method a tracer compound is a compound of the invention, or any of its enantiomers or any mixture thereof, an N oxide thereof, a pharmaceutically acceptable salt thereof, in a labelled or un-labelled form.

In a preferred embodiment the physical detection method is selected from PET, SPECT; MRS, MRI, CAT, or combinations thereof.

The labelled compound of the invention preferably contains at least one radionuclide as a label. Positron emitting radionuclides are all candidates for usage. In the context of this invention the radionuclide is preferably selected from $^2$H (deuterium), $^3$H (tritium), $^{11}$C, $^{13}$C $^{14}$C, $^{15}$O, $^{13}$N, $^{123}$I, $^{125}$I, $^{131}$I, $^{18}$F and $^{99m}$Tc.

An example of commercially available labelling agents, which can be used in the preparation of the labelled compounds of the present invention is [$^{11}$C]O$_2$, $^{18}$F, and NaI with different isotopes of Iodine.

In particular [$^{11}$C]O$_2$ may be converted to a [$^{11}$C]-methylating agent, such as [$^{11}$C]H$_3$I or [$^{11}$C]-methyl triflate.

Labelled compounds containing e.g. [$^{125}$I] labelled 1-iodoprop-1-en-3-yl as substituent on N-8, may be prepared as described in the art [Elmaleh, et al.; *J. Nucl. Med.* 1996 37 1197–1202].

Labelled compounds containing e.g. [$^{18}$F]-alkyl substituted N-8 may be prepared as described in the art, e.g. in WO 96/39198.

The tracer compound can be selected in accordance with the detection method chosen.

In one preferred embodiment, the labelled or unlabelled compound of the invention can be detected by a suitable spectroscopic method, in particular UV spectroscopy and/or fluorescence spectroscopy.

In anther preferred embodiment, the compounds of the invention labelled by incorporation of a isotope into the molecule, which may in particular be an isotope of the naturally occurring atoms including $^2$H (deuterium), $^3$H (tritium), $^{11}$C, $^{13}$C, $^{14}$C, $^{15}$O, $^{13}$N, $^{123}$I, $^{125}$I, $^{131}$I, $^{18}$F and $^{99m}$Tc, and the isotope incorporation may be measured by conventional scintillation counting techniques.

In a third preferred embodiment, the physical method for detecting said tracer compound of the present invention is selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Before conducting the method of the present invention, a diagnostically effective amount of a labelled or unlabelled compound of the invention is administered to a living body, including a human.

The diazabicycloalkane derivative of the invention is believed to be particularly suited for in vivo receptor imaging (neuroimaging).

In a preferred embodiment the diazabicycloalkane derivative of the invention for use as diagnostic tool or monitoring agent is 3-(6-Nitro-2-quinolinyl)-9-methyl-3,9-diazabicyclo-[4.2.1]-nonane, 3-(6-Nitro-2-quinolinyl)-9-H-3,9-diazabicyclo-[ 4.2.1]-nonane, 3-(6-Nitro-2-quinolinyl)-10-methyl-3,10-diazabicyclo-[4.2.1]-decane, 3-(6-Nitro-2-quinolinyl)-10-H-3,10-diazabicyclo-[4.2.1]-decane, or precursors thereof, or provided in a suitable labelled form.

In a particularly preferred embodiment the physical method for detecting the diazabicycloalkane derivative of the invention is Position Emission Tomography (PET).

It is currently believed that the diagnostically effective amount of the labelled or unlabelled compound of the invention, to be administered before conducting the in vivo method for the invention, is within a range of from 0.1 ng to 100 mg per kg body weight, preferably within a range of from 1 ng to 10 mg per kg body weight.

Pharmaceutical Compositions

In another aspect the invention provides novel pharmaceutical compositions comprising a therapeutically effective amount of the diazabicycloalkane derivatives of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicycloalkane derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient-per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The diazabicycloalkane derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of a diazabicycloalkane derivative of the invention.

In a preferred embodiment, the disease, disorder or condition relates to the central nervous system.

In a preferred embodiment, the disease, disorder or condition is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, -post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a another preferred embodiment, the disease, disorder or condition are associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In a third preferred embodiment, the disease, disorder or condition is related to the endocrine system, such as thyrotoxicosis, pheochromocytoma, hypertension and arrhythmias.

In a fourth preferred embodiment, the disease, disorder or condition is a neurodegenerative disorders, including transient anoxia and induced neuro-degeneration.

In a fifth preferred embodiment, the disease, disorder or condition is an inflammatory disorder, including inflammatory skin disorders such as acne and rosacea, Chron's disease, inflammatory bowel disease, ulcerative colitis, and diarrhoea.

In a sixth preferred embodiment, the disease, disorder or condition is mild, moderate or even severe pain of acute, chronic or recurrent character, as well as pain caused by migraine, postoperative pain, and phantom limb pain.

In a seventh preferred embodiment, the disease, disorder or condition is associated with withdrawal symptoms caused by termination of use of addictive substances, including nicotine containing products such as tobacco, opioids such as heroin, cocaine and morphine, benzodiazepines and benzodiazepine-like drugs, and alcohol.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Examples

General

All reactions involving air sensitive reagents or intermediates were performed under nitrogen and in anhydrous solvents. Magnesium sulphate was used as drying agent in the workup-procedures and solvents were evaporated under reduced pressure.

(±) 9-Methyl-3,9-diazabicyclo-[4.2.1]-nonane;

(±) 9-Benzyl-3,9-diazabicyclo-[4.2.1]-nonane; and (±) 10-Methyl-3,10-diazabicyclo-[4.3.1]-decane Were prepared according to [Michaels R J and Zaugg H E; *J. Org. Chem.* 1960 25 637].

(±) 3-(2-Naphthalyl)-9-methyl-3,9-diazabicyclo-[4.2.1]-nonane fumaric acid salt (1)

A mixture of 2-bromonaphtalene (5.0 g, 24.1 mmol), 9-methyl-3,9-diazabicyclo-[4.2.1]-nonane (3.38 g, 24.1 mmol) and palladacycle (0.045 g, 0.048 mmol) [*Angew. Chem. Int. Ed. Engl.* 1995 34 1844] was stirred for two days at 150° C. Sodium hydroxide (50 ml; 1 M) was added at room temperature. The mixture was extracted with diethyl ether (2×100 ml). Chromatography on silica gel with dichloromethane, methanol and conc. ammonia (89:10:1) gave the title compound. The corresponding salt was obtained by addition of a diethyl ether and methanol mixture (9:1) saturated with fumaric acid. Yield 0.30 g, 3%. Mp. 173–174° C.

(±) 3-(2-Naphthalyl)-9-H-3,9-diazabicyclo-[4.2.1]-nonane

Are prepared by demethylation of the corresponding 9-methyl-3,9-diazabicyclo-[4.2.1]-nonane.

(±) 3-(2-Naphthalyl)-10-Methyl-3,10-diazabicyclo-[4.3.1]-decane; and (±) 3-(2-Naphthalyl)-10-H-3,10-diazabicyclo-[4.2.1]-decane Are prepared in analogy from 10-methyl-3,10-diazabicyclo-[4.2.1]-decane.

(±) 3-(2-Quinolinyl)-9-methyl-3,9-diazabicyclo-[4.2.1]-nonane Fumaric Acid Salt (2)

A mixture of 2-chloroquinoline (5.0 g, 30.6 mmol) and 9-methyl-3,9-diazabicyclo-[4.2.1]-nonane (3.38 g, 24.1 mmol) was stirred in the absence of solvent for 4 h at 140°

C. Sodium hydroxide (50 ml; 1 M) was added at room temperature. The mixture was extracted with diethyl ether (2×100 ml). Chromatography on silica gel with dichloromethane, methanol and conc. ammonia (89:10:1) gave the title compound. The corresponding salt was obtained by addition of a diethyl ether and methanol mixture (9:1) saturated with fumaric acid. Yield 5.2 g, 44%. Mp. 173.0–174.2° C.

(±) 3-(2-Quinolinyl)-10-methyl-3,10-diazabicyclo-[4.3.1]-decane; and (±) 3-(2-Quinolinyl)-10-H-3,10-diazabicyclo-[4.3.1]-decane Are prepared in analogy from 10-methyl-3,10-diazabicyclo-[4.2.1]-decane.

Method A (±) 3-(3,4-Dichlorophenyl)-9-methyl-3,9-diazabicyclo-[4.2.1]-nonane fumaric acid salt (A1)

A mixture of 1-bromo-3,4-dichlorobenzene (6.65 g, 29.6 mmol) and 9-methyl-3,9-diazabicyclo-[4.2.1]-nonane (5.0 g, 35.5 mmol), potassium-tert-butoxide (6.64 g, 59.2 mmol), tetrakis triphenylphosphine palladium(0) (1.0 g, 0.88 mmol) and 1,2-dimethoxyethane (50 ml) was stirred overnight. Sodium hydroxide (50 ml; 1 M) was added at room temperature. The mixture was extracted with ethyl acetate (2×40 ml). Chromatography on silica gel with dichloromethane, methanol and conc. ammonia (89:10:1) gave the title compound, Yield 2.41 g, 29%. The corresponding salt was obtained by addition of a diethyl ether and methanol mixture (9:1) saturated with fumaric acid. Mp. 114.4° C.

(±) 3-(3,4-Dichlorophenyl)-10-methyl-3,10-diazabicyclo-[4.3.1]-decane; and (±) 3-(3,4-Dichlorophenyl)-10-H-3,10-diazabicyclo-[4.3.1]-decane Are prepared in analogy from 10-methyl-3,10-diazabicyclo-[4.2.1]-decane.

(±) 3-(6-Quinolinyl)-9-methyl-3,9-diazabicyclo-[4.2.1]-nonane Fumaric Acid Salt (A2)

Was prepared according to Method A, using 6-chloroquinoline as starting material and palladacycle [*Angew. Chem. Int. Ed. Engl.* 1995 34 1844], palladium acetate and 2-biphenyl-di-tert-butylphosphine as catalysts. Mp. 164–166° C.

(±) 3-(6-Quinolinyl)-9-H-3,9-diazabicyclo-[4.2.1]-nonane

Are prepared by demethylation of the corresponding 9-methyl-3,9-diazabicyclo-[4.2.1]-nonane.

(±) 3-(6-Quinolinyl)-10-H-3,10-diazabicyclo-[4.3.1]-decane; and (±) 3-(6-Quinolinyl)-10-methyl-3,10-diazabicyclo-[4.3.1]-decane Are prepared in analogy from 10-methyl-3,10-diazabicyclo-[4.2.1]-decane.

(±) 3-(4-Fluorophenyl)-9-methyl-3,9-diazabicyclo-[4.2.1]-nonane fumaric acid salt (A3)

Was prepared according to Method A, using 1-bromo-4-fluorobenzene as reactant. This product was separated from a reaction-mixture of 3-(3-fluorophenyl)-9-methyl-3,9-diazabicyclo-[4.2.1]-nonane and 3-(4-fluorophenyl)-9-methyl-3,9-diazabicyclo-[4.2.1]-nonane. Mp. 123.7° C.

(±) 3-(3-Fluorophenyl)-9-methyl-3,9-diazabicyclo-[4.2.1]-nonane fumaric acid salt (A4)

Was prepared according to Method A, using 1-bromo-4-fluorobenzene as reactant. This product was separated from a reaction-mixture of 3-(3-fluorophenyl)-9-methyl-3,9-diazabicyclo-[4.2.1]-nonane and 3-(4-fluorophenyl)-9-methyl-3,9-diazabicyclo-[4.2.1]-nonane. Mp. 138.6° C.

(±) 3-(4-Trifluoromethoxyphenyl)-9-methyl-3,9-diazabicyclo-[4.2.1]-nonane (A5)

Was prepared according to Method A, using 1-bromo-4-fluorobenzene as reactant. This product was separated from a reaction-mixture of 3-(3-trifluoromethoxyphenyl)-9-methyl-3,9-diazabicyclo-[4.2.1]-nonane and 3-(4-trifluoromethoxy-phenyl)-9-methyl-3,9-diazabicyclo-[4.2.1]-nonane. The product was isolated as an oil.

(±) 3-(3-Trifluoromethoxyphenyl)-9-methyl-3,9-diazabicyclo-[4.2.1]-nonane (A6)

Was prepared according to Method A, using 1-bromo-4-fluorobenzene as reactant. This product was separated from a reaction-mixture of 3-(3-trifluoromethoxyphenyl)-9-methyl-3,9-diazabicyclo-[4.2.1]-nonane and 3-(4-trifluoromethoxyphenyl)-9-methyl-3,9-diazabicyclo-[4.2.1]-nonane. The product was isolated as an oil.

(±) 3-(Phenyl)-9-methyl-3,9-diazabicyclo-[4.2.1]-nonane fumaric acid salt (A7)

Was prepared according to Method A. Mp. 143.9° C.

(±) 3-(3-Chlorophenyl)-9-methyl-3,9-diazabicyclo-[4.2.1]-nonane fumaric acid salt (A8)

Was prepared according to Method A. Amorphous material.

(±) 3-(3-Quinolinyl)-9-methyl-3,9-diazabicyclo-[4.2.1]-nonane fumaric acid salt (A9)

Was prepared according to Method A. Mp. 113.8–125.4° C.

(±) 3-(3-Bromophenyl)-9-methyl-3,9-diazabicyclo-[4.2.1]-nonane fumaric acid salt (A10)

Was prepared according to Method A. Mp. 88.6° C.

(±) 3-(4-Biphenylyl)-9-methyl-3,9-diazabicyclo-[4.2.1-nonane fumaric acid salt (A11)

Was prepared according to Method A. Mp. 178–181° C.

(±) 3-(5-Phenyl-2-thienyl)-9-methyl-3,9-diazabicyclo-[4.2.1]-nonane fumaric acid salt (A12)

Was prepared according to Method A. Mp. 135.4° C.

(±) 3-(2-Fluorenyl)-9-methyl-3,9-diazabicyclo-[4.2.1]-nonane fumaric acid salt (A13)

Was prepared according to Method A, using 2-bromofluorene as starting material and palladacycle [*Angew. Chem. Int. Ed. Enql.* 1995 34 1844], palladium acetate and 2-biphenyl-di-tert-butylphosphine as catalysts. Mp. 172.9° C.

(±) 3-(2-Fluorenyl)-9-H-3,9-diazabicyclo-[4.2.1]-nonane;

(±) 3-(2-Fluorenyl)-10-methyl-3,10-diazabicyclo-[4.3.1]-decane;

(±) 3-(2-Fluorenyl)-10-H-3,10-diazabicyclo-[4.3.1]-decane;

Are prepared in analogy.

(±) 3-(2-Fluoren-9-onyl)-9-H-3,9-diazabicyclo-[4.2.1]-nonane;

(±) 3-(2-Fluoren-9-onyl)-9-H-3,9-diazabicyclo-[4.2.1]-nonane;

(±) 3-(2-Fluoren-9-onyl)-10-methyl-3,10-diazabicyclo-[4.3.1]-decane;

(±) 3-(2-Fluoren-9-onyl)-10-H-3,10-diazabicyclo-[4.3.1]-decane

Are prepared in analogy by method A from 2-bromofluorenone.

Method B (±) 3-(3,4-Dichlorophenyl)-9-H-3,9-diazabicyclo-4.2.1]-nonane fumaric acid salt (B1)

A mixture of 3-(3,4-Dichlorophenyl)-9-methyl-3,9-diazabicyclo-[4.2.1]-nonane (0.50 g, 1.8 mmol), 1-chloroethylchloroformate (0.63 g, 4.4 mmol) and xylene (10 ml) was stirred at reflux for 24 h, methanol (10 ml) was added and the mixture was stirred at reflux for 5 hours. Sodium hydroxide (50 ml; 1 M) was added at room temperature. The mixture was extracted with ethyl acetate (2×40 ml). Chromatography on silica gel with dichloromethane, methanol and conc. ammonia (89:10:1) gave the title compound. Yield 0.14 g, 29%. The corresponding salt was obtained by addition of a diethyl ether and methanol mixture (9:1) saturated with fumaric acid. Mp. 222.3° C.

(±) 3-Phenyl-9-H-3,9-diazabicyclo-[4.2.1]-nonane Fumaric Acid Salt (B2)

Was prepared according to Method B. Mp. 216.5° C.

(±) 3-(3-Chlorophenyl)-9-H-3,9-diazabicyclo-[4.2.1]-nonane fumaric acid salt (B3)

Was prepared according to Method B. Mp. 181.0–182.3° C.

(±) 3-(4-Biphenylyl)-9-H-3,9-diazabicyclo-[4.2.1]-nonane fumaric acid salt (B4)

Was prepared according to Method B. Mp. 212–215° C.

(±) 3-(3-Quinolinyl)-9-H-3,9-diazabicyclo-[4.2.1]-nonane Fumaric Acid (B5)

A mixture of (±) 3-(3-quinolinyl)-9-methyl-3,9-diazabicyclo-[4.2.1]-nonane (2.77 g, 10.4 mmol), diethyl azodicarboxylate (8.2 ml, 51.8 mmol) and toluene (50 ml) was stirred at 95° C. for 75 min. Aqueous sodium hydroxide (50 ml; 1 M) was added and the mixture was extracted five times with diethyl ether (5×30 ml). The crude mixture was purified by chromatography on silica gel with dichloromethane, methanol and conc. ammonia (89:10:1) gave the title compound as free base. The corresponding salt was obtained by addition of a diethyl ether and methanol mixture (9:1) saturated with fumaric acid. Yield 0.77 g, 29%. Mp. 195.9° C.

(±) 3-1[(5-Chloropyrid-3-yl)-5-oxyethoxypyrid-3-yl]-9-Methyl-3,9-diazabicyclo-[4.2.1]-nonane (B6), and (±) O,O'-bis-[5-(9-Methyl-3,9-diazabicyclo-[4.2.1]-nonan-3-yl)-3-pyridyl]-ethyleneglycol fumaric acid salt (B7)

A mixture of O,O'-bis-(5-chloro-3-pyridyl)-ethyleneglycol (2.0 g, 7.0 mmol), 9-methyl-3,9-diazabicyclo-[4.2.1]-nonane (3.9 g, 28.1 mmol), cecium carbonate (4.6 g, 14.0 mmol), palladacycle (0.050 g, 0.053 mmol), palladium acetate (0.050 g, 0.22 mmol), 2-biphenyl-di-tert-butyl-phosphine (0.05 g, 0.17 mmol) and tri-tert-butylphophine (0.05 g, 0.25 mmol) was stirred at 130° C. overnight. Aqueous sodium hydroxide (50 ml; 1 M) was added and the mixture was extracted five times with diethylether (5×30 ml). The crude mixture was evaporated and purified by chromatography on silica gel with dichloromethane, methanol and conc. ammonia (89:10:1) gave the title compound (A) as free base in chronological order. Yield 0.40 g, 20%. Mp. 112–113° C., and (B) yield 0.40 g, 15%. The corresponding salt of B was obtained by addition of a diethyl ether and methanol mixture (9:1) saturated with fumaric acid. Mp. 84–88° C.

(±) O,O'-bis-(5-chloro-3-pyridyl)-ethyleneglycol

A mixture of ethyleneglycol (138.4 g, 2.23 mol) and sodium (12.3 g, 0.53 mol) was stirred at 80° C. for 4 hours. 3,5-Dichloropyridine (66.0 g, 0.45 mol) and dimethyl sulfoxide (300 ml) was stirred at 110° C. for 10 hours. The mixture was allowed to reach room temperature. Aqueous sodium hydroxide (1 M; 600 ml) was added, the mixture was stirred and filtered. The title compound was isolated as a crystalline product was isolated (8.7 g, 6.8%). Mp. 136–138° C.

Method C (±) 3-(4-Methyl-2-quinolinyl)-9-methyl-3,9-diazabicyclo-[4.2.1]-nonane fumaric acid salt (C1)

A neat mixture of 4-methyl-2-chloroquinoline (6.33 g, 35.7 mmol) and 9-methyl-3,9-diazabicyclo-[4.2.1]-nonane (5.0 g, 35.5 mmol) was stirred at 140° C. for 2.5 hours. The mixture was allowed to cool to room temperature. Aqueous sodium hydroxide (100 ml, 1 M) was added and the mixture was extracted with diethyl ether (3×100 ml). The crude mixture was purified by chromatography on silica gel with dichloromethane, methanol and conc. ammonia (89:10:1) gave the title compound as free base. Yield 5.77 g, 100%. The corresponding salt was obtained by addition of a diethyl ether and methanol mixture (9:1) saturated with fumaric acid. Mp. 179.3° C.

(±) 3-(6-Phenyl-3-pyridazinyl)-9-methyl-3,9-diazabicyclo-[4.2.1]-nonane fumaric acid salt (C2)

Was prepared according to Method C using 120° C. as reaction temperature. Mp. 140–141° C.

(±) 3-(6-Nitro-2-quinolinyl)-9-methyl-3,9-diazabicyclo-[4.2.1]-nonane free base (C3)

Was prepared according to Method C using dioxane as solvent at reflux temperature. Mp. 148.1–1499° C.

(±) 3-(6-Phenyl-3-pyridazinyl)-10-methyl-3,10-diazabicyclo-[4.3.1]-decane fumaric acid salt (C4)

Was prepared according to Method C from 10-methyl-3,10-diazabicyclo-[4.3.1]-decane using 120° C. as reaction temperature. Mp. 140.8–148.0° C.

(±) 3-(4-Nitrophenyl)-9-methyl-3,9-diazabicyclo-[4.2.1]-nonane fumaric acid salt (C5)

Was prepared according to Method C. Mp. 196.1° C.

(±) 3-(4-Trifluoromethylphenyl)-9-methyl-3,9-diazabicyclo-[4.2.1]-nonane fumaric acid salt (C6)

Was prepared according to Method C, at 180° C. in a sealed vessel, due to the volatility of the starting material. Mp. 165.0° C.

(±) 3-(4-Aminophenyl)-9-methyl-3,9-diazabicyclo-[4.2.1]-nonane fumaric acid salt (C7)

Was prepared by catalytic hydrogenation of (±) 3-(4-nitrophenyl)-9-methyl-3,9-diazabicyclo-[4.2.1]-nonane, with palladium on carbon as catalyst. Mp. 91–93° C.

(±) 3-(4-Acetylaminophenyl)-9-methyl-3,9-diazabicyclo-[4.2.1]-nonane fumaric acid salt (C8)

Was prepared by acetylation of (±) 3-(4-aminophenyl)-9-methyl-3,9-diazabicyclo-[4.2.1]-nonane, using acetic acid anhydride as reagent and dichloromethane as solvent. Mp. 130.0–132.4° C.

(±) 3-[4-(N-Pyrrolidinylphenyl)]1-9-methyl-3,9-diazabicyclo-[4.2.1]-nonane fumaric acid salt (C9)

Was prepared from (±) 3-(4-aminophenyl)-9-methyl-3,9-diazabicyclo-[4.2.1]-nonane, 1,4-dibromo-butane, potassium carbonate and dimethylformamide as solvent at 80° C. Mp. 141.5–143.6° C.

Method D (±) 3-(6-Bromo-3-pyridyl)-10-methyl-3,10-diazabicyclo-[4.3.1]-decane fumaric acid salt (D1); and (±) 3-(6-Bromo-3-pyridyl)-10-H-3,10-diazabicyclo-[4.3.1]-decane fumaric acid salt (D2)

A mixture of 3-(3-pyridyl)-10-methyl-3,10-diazabicyclo-[4.3.1]-decane (2.15 g, 8.8 mmol), NBS (1.57 g, 8.8 mmol) and acetonitrile (50 ml) was stirred at 0° C. for 2 hours. Aqueous sodium hydroxide (30 ml, 1 M) was added. The acetonitrile was evaporated. The mixture was extracted with diethyl ether (2×50 ml). The crude mixture purified by chromatography on silica gel with dichloromethane, methanol and conc. ammonia (89:10:1) gave the title compounds as free base. The compounds were eluated and were collected in the mentioned order. (3-(6-Bromo-3-pyridyl)-10-methyl-3,10-diazabicyclo-[4.3.1]-decane). Yield 0.40 g, 15%. The corresponding salt was obtained by addition of a diethyl ether and methanol mixture (9:1) saturated with fumaric acid. Mp. 179.0° C., (3-(6-Bromo-3-pyridyl)-10-H-

3,10-diazabicyclo-[4.3.1]-decane). Yield 0.16 g, 6%. The corresponding salt was obtained by addition of a diethyl ether and methanol mixture (9:1) saturated with fumaric acid. Mp. 209.6–214.6° C.

(±) 3-(3-Pyridyl)-10-H-3,10-diazabicyclo-[4.3.1]-decane fumaric acid salt (D3)

Was prepared by Method D from 3-(3-pyridyl)-10-methyl-3,10-diazabicyclo-[4.3.1]-decane, using NIS (instead of NBS), resulting in demethylation and no halogenation. Mp. 179.7–183.3° C.

(±) 3-(6-Phenyl-3-pyridyl)-10-H-3,10-diazabicyclo-[4.3.1]-decane fumaric acid salt (D4)

Was prepared by Method D from 3-(6-phenyl-3-pyridyl)-10-methyl-3,10-diazabicyclo-[4.3.1]-decane, using NIS (instead of NBS), resulting in demethylation and no halogenation. Mp. 185° C.

(±) 3-(6-Nitro-2-quinolinyl)-9-H-39-diazabicyclo-[4.2.1]-nonane Free Base (D5)

Was prepared according to Method D using NIS (instead of NBS), resulting in demethylation and no halogenation.

Method E (±) 3-(3-Pyridyl)-10-methyl-3,10-diazabicyclo-[4.3.1]-decane fumaric acid salt (E1)

A mixture of 3-fluoropyridine (8.74 g, 90 mmol) and 10-methyl-3,10-diazabicyclo-[4.3.1]-decane (13.9 g, 90 mmol) was stirred at 180° C. for 48 hours. Aqueous sodium hydroxide (50 ml, 1 M) was added at room temperature and the mixture was extracted with diethyl ether (2×100 ml). Purification by column chromatography on silica gel with dichloromethane, methanol and conc. ammonia (89:10:1) yielded 26% of the free base (5,5 g, 24 mmol) as an oil, which was converted to the corresponding fumaric acid salt. Mp. 144.4–154.4° C.

(±) 3-(3-Pyridyl)-9-methyl-3,9-diazabicyclo-[4.2.1]-nonane fumaric acid salt (E2)

Was prepared according to Method E from 9-methyl-3,9-diazabicyclo[4.2.1]-nonane. Mp. 170–172° C.

(±) 3-(6-Chloro-3-pyridyl)-10-methyl-3,10-diazabicyclo-[4.3.1]-decane fumaric acid salt (E3)

A mixture of 3-(6-bromo-3-pyridyl)-10-methyl-3,10-diazabicyclo-[4.3.1]-decane (0.52 g, 1.7 mmol), conc. hydrochloric acid (20 ml) and potassium chloride (5 g) was heated at reflux for 21 days. Aqueous sodium hydroxide (30 ml, 1 M) was added. The mixture was extracted with ethyl acetate (2×40 ml). Purification by column chromatography on silica gel with dichloromethane, methanol and conc. ammonia (89:10:1) yielded 0.29 g, 6% of the free base. The corresponding salt was obtained by addition of a diethyl ether and methanol mixture (9:1) saturated with fumaric acid. Mp. 170–174° C.

Method F (±) 3-[6-(2-Toluyl)-3-pyridyl]-9-methyl-3,9-diazabicyclo-[4.2.1]-nonane fumaric acid salt (F1)

A mixture of 3-(6-bromo-3-pyridyl)-9-methyl-3,9-diazabicyclo-[4.2.1]-nonane (0.50 g, 1.7 mmol), o-toluylboronic acid (0.35 g, 2.55 mmol), aqueous potassium carbonate (2.6 ml, 1.7 mmol), 1,3-propandiol (0.37 ml, 5.1 mmol), palladacycle (16 mg, 0.017 mmol) [Angew. Chem. Int. Ed. Engl. 1995 34 18441, palladium acetate (7.6 mg, 0.034 mmol) and tri-teri-butylphosphine (6.8 mg, 0.034 mmol) and dioxane (2 ml) was stirred at 110° C. for 3 hours. Aqueous sodium hydroxide (5 ml, 1 M) was added. The mixture was extracted with ethyl acetate (2×4 ml). Purification by column chromatography on silica gel with dichloromethane, methanol and conc. ammonia (89:10:1) yielded 0.35 g, 68% of the free base. The corresponding salt was obtained by addition of a diethyl ether and methanol mixture (9:1) saturated with fumaric acid. Mp. 155.2–160.5° C.

(±) 3-[6-(2-Methoxy-phenyl)-3-pyridyl]-9-methyl-3,9-diazabicyclo-[4.2.1]-nonane fumaric acid salt (F2)

Was prepared according to Method F from 3-(6-bromo-3-pyridyl)-9-methyl-3,9-diazabicyclo-[4.2.1]-nonane. Mp. 87.7° C.

(±) 3-6-(4-Dimethylaminosulfonyl-phenyl]-3-pyridyl]-9-methyl-3,9-diazabicyclo-[4.2.1]-nonane fumaric acid salt (F3)

Was prepared according to Method F from 3-(6-bromo-3-pyridyl)-9-methyl-3,9-diazabicyclo-[4.2.1]-nonane. Mp. 165.0° C.

(±) 3-[6-(2-Benzothiophenyl)-3-pyridyl]-9-methyl-3,9-diazabicyclo-[4.2.1]-nonane fumaric acid salt (F4)

Was prepared according to Method F from 3-(6-bromo-3-pyridyl)-9-methyl-3,9-diazabicyclo-[4.2.1]-nonane. Mp. 190.1° C.

(±) 3-[6-(3-Thienyl)-3-pyridyl]-9-methyl-3,9-diazabicyclo-[4.2.1]-nonane fumaric acid salt (F5)

Was prepared according to Method F from 3-(6-bromo-3-pyridyl)-9-methyl-3,9-diazabicyclo-[4.2.1]-nonane. Mp. 160.9–165.5° C.

(±) 3-[6-(3-Pyridyl)-3-pyridyl]-9-methyl-3.9-diazabicyclo-[4.2.1]-nonane fumaric acid salt (F6)

Was prepared according to Method F from 3-(6-bromo-3-pyridyl)-9-methyl-3,9-diazabicyclo-[4.2.1]-nonane. Mp. 158.9–161.8° C.

(±) 3-[6-(3-Nitrophenyl)-3-pyridyl]-9-methyl-3,9-diazabicyclo-[4.2.1]-nonane fumaric acid salt (F7)

Was prepared according to Method F from 3-(6-bromo-3-pyridyl)-9-methyl-3,9-diazabicyclo-[4.2.1]-nonane. Mp. 205.0–206.9° C.

(±) 5,5'-Bis-3-(9-methyl-3,9-diazabicyclo-[4.2.1]-nonanyl)-2,2'-bipyridyl (F8)

A mixture of 3-(6-bromopyridyl)-9-methyl-3,9-diazabicyclo-[4.2.1]-nonane (1.0 g, 3.4 mmol), hexamethylditin (0.35 ml, 1.7 mmol), tetrakis triphenylphosphine palladium (0) (78 mg, 0.068 mmol), cesium fluoride (1.0 g, 6.8 mmol) and dioxane (10 ml) was stirred at reflux overnight. Aqueous sodium hydroxide (5 ml, 1 M) was added. The mixture was extracted with ethyl acetate (2×4 ml). Purification by column chromatography on silica gel with dichloromethane, methanol and conc. ammonia (89:10:1) yielded 0.36 g, 50% of the free base. The corresponding salt was obtained by addition of a diethyl ether and methanol mixture (9:1) saturated with fumaric acid. Mp. 206–208° C.

(±) 3-Acetyl-9-benzyl-3,9-diazabicyclo-[4.2.1]-nonane

A mixture of 9-benzyl-3,9-diazabicyclo-[4.2.1]-nonane (5.0 g, 23.1 mmol), acetic acid anhydride (3.54 g, 34.7 mmol) and dichloromethane (50 ml) was stirred for 3 h at room temperature. The mixture was evaporated and aqueous sodium hydroxide (20 ml, 1 M) was added. The mixture was extracted with ethyl acetate (4×30 ml). The crude product was isolated. Yield 5.96 g, 100%.

(±) 3-Acetyl-9-H-3,9-diazabicyclo-[4.2.1]-nonane

A mixture of 3-acetyl-9-benzyl-3,9-diazabicyclo-[4.2.1]-nonane (5.9 g, 22.8 mmol), palladium on carbon (0.60 g, 5%) and ethanol (100 ml) was stirred under hydrogen for 24 hours. The crude product was purified by column chromatography on silica gel with dichloromethane, methanol and conc. ammonia (89:10:1) yielded 2.73 g, 71% of the free base.

(±) 3-Acetyl-9-(6-phenyl-3-pyridazinyl)-3,9-diazabicyclo-[4.2.1]-nonane

A mixture of 3-acetyl-9-H-3,9-diazabicyclo-[4.2.1]-nonane (1.22 g, 7.3 mmol), 3-chloro-6-phenylpyridazine (1.38 g, 7.3 mmol) and dioxane (10 ml) was stirred at reflux overnight. Purification by column chromatography on silica gel with dichloromethane, methanol and conc. ammonia (89:10:1) yielded 0.50 g, 21% of the free base.

(±) 3-H-9-(6-Phenyl-3-pyridazinyl)-3,9-diazabicyclo-[4.2.1]-nonane fumaric acid salt (F9)

A mixture of 3-acetyl-9-(6-phenyl-3-pyridazinyl)-3,9-diazabicyclo-[4.2.1]-nonane (0.50 g, 1.6 mmol) and conc. hydrochloric acid was stirred at reflux for 7 days. The mixture was evaporated and aqueous sodium hydroxide (30 ml, 1 M) was added. The mixture was extracted with dichloromethane (3×30 ml). Purification by column chromatography on silica gel with dichloromethane, methanol and conc. ammonia (89:10:1) yielded 0.26 g, 58% of the free base. The corresponding salt was obtained by addition of a diethyl ether and methanol mixture (9:1) saturated with fumaric acid. Mp. 222.0° C.

(±) 3-Methyl-9-(6-phenyl-3-pyridazinyl)-3,9-diazabicyclo-[4.2.1]-nonane fumaric acid salt (F10)

A mixture of 3-H-9-(6-phenyl-3-pyridazinyl)-3,9-diazabicyclo-[4.2.1]-nonane (0.15 g, 0.53 mmol), formic acid (5 ml) and formalin (5 ml) was stirred at reflux for 1 hour. The mixture was evaporated. Aqueous sodium hydroxide (20 ml, 1 M) was added and the mixture was extracted with ethyl acetate (3×30 ml). Purification by column chromatography on silica gel with dichloromethane, methanol and conc. ammonia (89:10:1) yielded 0.14 g, 88% of the free base. The corresponding salt was obtained by addition of a diethyl ether and methanol mixture (9:1) saturated with fumaric acid. Mp. 153.8° C.

From the starting materials used above the following compounds are prepared:

(±) 3-(6-Phenylthio-3-pyridyl)-9-H-3,9-diazabicyclo-[4.2.1]-nonane;
(±) 3-(6-Phenylthio-3-pyridyl)-9-methyl-3,9-diazabicyclo-[4.2.1]-nonane;
(±) 3-(6-Phenylthio-3-pyridyl)-10-H-3,10-diazabicyclo-[4.3.1]-decane;
(±) 3-(6-Phenylthio-3-pyridyl)-10-methyl-3,10-diazabicyclo-[4.3.1]-decane;
(±) 3-(6-Pyrid-2-ylthio-3-pyridyl)-9-H-3,9-diazabicyclo-[4.2.1]-nonane;
(±) 3-(6-Pyrid-2-ylthio-3-pyridyl)-9-methyl-3,9-diazabicyclo-[4.2.1]-nonane;
(±) 3-(6-Pyrid-2-ylthio-3-pyridyl)-10-H-3,10-diazabicyclo-[4.3.1]-decane;
(±) 3-(6-Pyrid-2-ylthio-3-pyridyl)-10-methyl-3,10-diazabicyclo-[4.3.1]-decane;
(±) 3-(6-Pyrid-3-ylthio-3-pyridyl)-9-H-3,9-diazabicyclo-[4.2.1]-nonane;
(±) 3-(6-Pyrid-3-ylthio-3-pyridyl)-9-methyl-3,9-diazabicyclo-[4.2.1]-nonane;
(±) 3-(6-Pyrid-3-ylthio-3-pyridyl)-10-H-3,10-diazabicyclo-[4.3.1]-decane;
(±) 3-(6-Pyrid-3-ylthio-3-pyridyl)-10-methyl-3,10-diazabicyclo-[4.3.1]-decane;
(±) 3-(6-Pyrid-4-ylthio-3-pyridyl)-9-H-3,9-diazabicyclo-[4.2.1]-nonane;
(±) 3-(6-Pyrid-4-ylthio-3-pyridyl)-9-methyl-3,9-diazabicyclo-[4.2.1]-nonane;
(±) 3-(6-Pyrid-4-ylthio-3-pyridyl)-10-H-3,10-diazabicyclo-[4.3.1]-decane;
(±) 3-(6-Pyrid-4-ylthio-3-pyridyl)-10-methyl-3,10-diazabicyclo-[4.3.1]-decane;
(±) 3-(6-Phenylsulfonyl-3-pyridyl)-9-H-3,9-diazabicyclo-[4.2.1]-nonane;
(±) 3-(6-Phenylsulfonyl-3-pyridyl)-9-methyl-3,9-diazabicyclo-[4.2.1]-nonane;
(±) 3-(6-Phenylsulfonyl-3-pyridyl)-10-H-3,10-diazabicyclo-[4.3.1]-decane;
(±) 3-(6-Phenylsulfonyl-3-pyridyl)-10-methyl-3,10-diazabicyclo-[4.3.1]-decane;
(±) 3-(6-Pyrid-2-ylsulfonyl-3-pyridyl)-9-H-3,9-diazabicyclo-[4.2.1]-nonane;
(±) 3-(6-Pyrid-2-ylsulfonyl-3-pyridyl)-9-methyl-3,9-diazabicyclo-[4.2.1]-nonane;
(±) 3-(6-Pyrid-2-ylsulfonyl-3-pyridyl)-10-H-3,10-diazabicyclo-[4.3.1]-decane;
(±) 3-(6-Pyrid-2-ylsulfonyl-3-pyridyl)-10-methyl-3,10-diazabicyclo-[4.3.1]-decane;
(±) 3-(6-Pyrid-3-ylsulfonyl-3-pyridyl)-9-H-3,9-diazabicyclo-[4.2.1]-nonane;
(±) 3-(6-Pyrid-3-ylsulfonyl-3-pyridyl)-9-methyl-3,9-diazabicyclo-[4.2.1]-nonane;
(±) 3-(6-Pyrid-3-ylsulfonyl-3-pyridyl)-10-H-3,10-diazabicyclo-[4.3.1]-decane;
(±) 3-(6-Pyrid-3-ylsulfonyl-3-pyridyl)-10-methyl-3,10-diazabicyclo-[4.3.1]-decane;
(±) 3-(6-Pyrid-4-ylthio-3-pyridyl)-9-H-3,9-diazabicyclo-[4.2.1]-nonane;
(±) 3-(6-Pyrid-4-ylthio-3-pyridyl)-9-methyl-3,9-diazabicyclo-[4.2.1]-nonane;
(±) 3-(6-Pyrid-4-ylthio-3-pyridyl)-10-H-3,10-diazabicyclo-[4.3.1]-decane;
(±) 3-(6-Pyrid-4-ylthio-3-pyridyl)-10-methyl-3,10-diazabicyclo-[4.3.1]-decane;
(±) 3-(6-Phenylamino-3-pyridyl)-9-H-3,9-diazabicyclo-[4.2.1]-nonane;
(±) 3-(6-Phenylamino-3-pyridyl)-9-methyl-3,9-diazabicyclo-[4.2.1]-nonane;
(±) 3-(6-Phenylamino-3-pyridyl)-10-H-3,10-diazabicyclo-[4.3.1]-decane;
(±) 3-(6-Phenylamino-3-pyridyl)-10-methyl-3,10-diazabicyclo-[4.3.1]-decane;
(±) 3-(6-Pyrid-2-ylamino-3-pyridyl)-9-H-3,9-diazabicyclo-[4.2.1]-nonane;
(±) 3-(6-Pyrid-2-ylamino-3-pyridyl)-9-methyl-3,9-diazabicyclo-[4.2.1]-nonane;
(±) 3-(6-Pyrid-2-ylamino-3-pyridyl)-10-H-3,10-diazabicyclo-[4.3.1]-decane;
(±) 3-(6-Pyrid-2-ylamino-3-pyridyl)-10-methyl-3,10-diazabicyclo-[4.3.1]-decane;
(±) 3-(6-Pyrid-3-ylamino-3-pyridyl)-9-H-3,9-diazabicyclo-[4.2.1]-nonane;
(±) 3-(6-Pyrid-3-ylamino-3-pyridyl)-9-methyl-3,9-diazabicyclo-[4.2.1]-nonane;
(±) 3-(6-Pyrid-3-ylamino-3-pyridyl)-10-H-3,10-diazabicyclo-[4.3.1]-decane;
(±) 3-(6-Pyrid-3-ylamino-3-pyridyl)-10-methyl-3,10-diazabicyclo-[4.3.1]-decane;
(±) 3-(6-Pyrid-4-ylamino-3-pyridyl)-9-H-3,9-diazabicyclo-[4.2.1]-nonane;
(±) (3-(6-Pyrid-4-ylamino-3-pyridyl)-9-methyl-3,9-diazabicyclo-[4.2.1]-nonane;
(±) 3-(6-Pyrid-4-ylamino-3-pyridyl)-10-H-3,10-diazabicyclo-[4.3.1]-decane;
(±) 3-(6-Pyrid-4-ylamino-3-pyridyl)-10-methyl-3,10-diazabicyclo-[4.3.1]-decane;
(±) 3-(6-Phenyl-acetylamino-3-pyridyl)-9-H-3,9-diazabicyclo-[4.2.1]-nonane;
(±) 3-(6-Phenyl-acetylamino-3-pyridyl)-9-methyl-3,9-diazabicyclo-[4.2.1]-nonane;

(±) 3-(6-Phenyl-acetylamino-3-pyridyl)-10-H-3,10-diazabicyclo-[4.3.1]-decane;
(±) 3-(6-Phenyl-acetylamino-3-pyridyl)-10-methyl-3,10-diazabicyclo-[4.3.1]-decane;
(±) 3-(6-Pyrid-2-yl-acetylamino-3-pyridyl)-9-H-3,9-diazabicyclo-[4.2.1]-nonane;
(±) 3-(6-Pyrid-2-yl-acetylamino-3-pyridyl)-9-methyl-3,9-diazabicyclo-[4.2.1]-nonane;
(±) 3-(6-Pyrid-2-yl-acetylamino-3-pyridyl)-10-H-3,10-diazabicyclo-[4.3.1]-decane;
(±)3-(6-Pyrid-2-yl-acetylamino-3-pyridyl)-10-methyl-3,10-diazabicyclo-[4.3.1]-decane;
(±) 3-(6-Pyrid-3-yl-acetylamino-3-pyridyl)-0.9-H-3,9-diazabicyclo-[4.2.1]-nonane;
(±) 3-(6-Pyrid-3-yl-acetylamino-3-pyridyl)-9-methyl-3,9-diazabicyclo-[4.2.1]-nonane;
(±) 3-(6-Pyrid-3-yl-acetylamino-3-pyridyl)-10-H-3,10-diazabicyclo-[4.3.1]-decane;
(±)3-(6-Pyrid-3-yl-acetylamino-3-pyridyl)-10-methyl-3,10-diazabicyclo-[4.3.1]-decane;
(±) 3-(6-Pyrid-4-yl-acetylamino-3-pyridyl)-9-H-3,9-diazabicyclo-[4.2.1]-nonane;
(±) 3-(6-Pyrid-4-yl-acetylamino-3-pyridyl)-9-methyl-3,9-diazabicyclo-[4.2.1]-nonane;
(±) 3-(6-Pyrid-4-yl-acetylamino-3-pyridyl)-10-H-3,10-diazabicyclo-[4.3.1]-decane;
(±)3-(6-Pyrid-4-yl-acetylamino-3-pyridyl)-10-methyl-3,10-diazabicyclo-[4.3.1]-decane;
(±) 3-(6-Phenoxy-3-pyridyl)-9-H-3,9-diazabicyclo-[4.2.1]-nonane;
(±) 3-(6-Phenoxy-3-pyridyl)-9-methyl-3,9-diazabicyclo-[4.2.1]-nonane;
(±) 3-(6-Phenoxy-3-pyridyl)-10-H-3,10-diazabicyclo-[4.3.1]-decane;
(±) 3-(6-Phenoxy-3-pyridyl)-10-methyl-3,10-diazabicyclo-[4.3.1]-decane;
(±) 3-(6-Pyrid-2-y-oxy-3-pyridyl)-9-H-3,9-diazabicyclo-[4.2.1]-nonane;
(±) 3-(6-Pyrid-2-yl-oxy-3-pyridyl)-9-methyl-3,9-diazabicyclo-[4.2.1]-nonane;
(±) 3-(6-Pyrid-2-yl-oxy-3-pyridyl)-10-H-3,10-diazabicyclo-[4.3.1]-decane;
(±) 3-(6-Pyrid-2-yl-oxy-3-pyridyl)-10-methyl-3,10-diazabicyclo-[4.3.1]-decane;
(±) 3-(6-Pyrid-3-y-oxy-3-pyridyl)-9-H-3,9-diazabicyclo-[4.2.1]-nonane;
(±) 3-(6-Pyrid-3-y-oxy-3-pyridyl)-9-methyl-3,9-diazabicyclo-[4.2.1]-nonane;
(±) 3-(6-Pyrid-3-yl-oxy-3-pyridyl)-10-H-3,10-diazabicyclo-[4.3.1]-decane;
(±) 3-(6-Pyrid-3-yl-oxy-3-pyridyl)-10-methyl-3,10-diazabicyclo-[4.3.1]-decane;
(±) 6-Pyrid-4-yl-oxy-3-pyridyl)-9-H-3,9-diazabicyclo-[4.2.1]-nonane;
(±) 3-(6-Pyrid-4-yl-oxy-3-pyridyl)-9-methyl-3,9-diazabicyclo-[4.2.1]-nonane;
(±) 3-(6-Pyrid-4-yl-oxy-3-pyridyl)-10-H-3,10-diazabicyclo-[4.3.1]-decane;
(±) 3-(6-Pyrid-4-yl-oxy-3-pyridyl)10-methyl-3,10-diazabicyclo-[4.3.1]-decane;
(±) 3-[2-(1,8-Naphtyridinyl)]-9-H-3,9-diazabicyclo-[4.2.1]-nonane;
(±) 3-[2-(1,8-Naphtyridinyl)]-9-methyl-3,9-diazabicyclo-[4.2.1]-nonane;
(±) 3-[2-(1,8-Naphtyridinyl)]-10-H-3,10-diazabicyclo-[4.3.1]-decane;
(±) 3-[2-(1,8-Naphtyridinyl)]-10-methyl-3,10-diazabicyclo-[4.3.1]-decane;
(±) 3-[2-(1,5-Naphtyridinyl)]-9-H-3,9-diazabicyclo-[4.2.1]-nonane;
(±) 3-[2-(1,5-Naphtyridinyl)]-9-methyl-3,9-diazabicyclo-[4.2.1]-nonane;
(±) 3-[2-(1,5-Naphtyridinyl)]-10-H-3,10-diazabicyclo-[4.3.1]-decane;
(±) 3-[2-(1,5-Naphtyridinyl)]-10-methyl-3,10-diazabicyclo-[4.3.1]-decane;
(±) 3-[2-(N-Methyl-carbazolyl)]-9-H-3,9-diazabicyclo-[4.2.1]-nonane;
(±) 3-[2-(N-Methyl-carbazolyl)]-9-methyl-3,9-diazabicyclo-[4.2.1]-nonane;
(±) 3-[2-(N-Methyl-carbazolyl)]-10-H-3,10-diazabicyclo-[4.3.1]-decane;
(±) 3-[2-(N-Methyl-carbazolyl)]-10-methyl-3,10-diazabicyclo-[4.3.1]-decane;
3-(2-Dibenzothiophenyl)-9-H-3,9-diazabicyclo-[4.2.1]-nonane;
(±) 3-(2-Dibenzothiophenyl)-9-methyl-3,9-diazabicyclo-[4.2.1]-nonane;
(±) 3-(2-Dibenzothiophenyl)-10-H-3,10-diazabicyclo-[4.3.1]-decane;
(±) 3-(2-Dibenzothiophenyl)-10-methyl-3,10-diazabicyclo-[4.3.1]-decane;
(±) 3-(2-Dibenzofuryl)-9-H-3,9-diazabicyclo-[4.2.1]-nonane;
(±) 3-(2-Dibenzofuryl)-9-methyl-3,9-diazabicyclo-[4.2.1]-nonane;
(±) 3-(2-Dibenzofuryl)-10-H-3,10-diazabicyclo-[4.3.1]-decane; and
(±) 3-(2-Dibenzofuryl)-10-methyl-3,10-diazabicyclo-[4.3.1]-decane.

Example 2

Biological Activity

In Vitro Inhibition of $^3$H-5-hydroxytryptamine ($^3$H-5-HT, Serotonin) Uptake in Cortical Synaptosomes Serotonin transporters/uptake sites on nerve terminals presumably function to terminate neuronal signaling by removing serotonin from the synaptic cleft. The activity of the serotonin transporter integral protein can be measured in vitro by synaptosomal uptake of $^3$H-5-hydroxytryptamine.

Preparations are performed at 0–4° C. unless otherwise indicated. Cerebral cortices from male Wistar rats (150–200 g) are homogenized for 5–10 sec in 100 volumes of ice-cold 0.32M sucrose containing 1 mM pargyline using a motor driven teflon pestle in a glass homogenizing vessel. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (1000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Aliquots of 4.0 ml tissue suspension are added to 100 pi of test solution and 100 μl of $^3$H-5-HT (1 nM, final concentration), mixed and incubated for 30 min at 37° C. Non-specific uptake is determined using citalopram (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-5-HT by 50%).

$$IC_{50} = \text{(applied test substance concentration, μM)} \times \frac{1}{\left(\frac{C_0}{C_x} - 1\right)}$$

where $C_0$ is specific binding in control assays and $C_x$ is the specific binding in the test assay (the calculations assume normal mass-action kinetics).

The results are presented in Table 1 below.

TABLE 1

| Compound | Compound No. | $^3$H-noradrenaline ($^3$H-NA) uptake $IC_{50}$ (μM) |
| --- | --- | --- |
| 3-(2-Quinolinyl)-9-methyl-3,9-diazabicyclo-[4.2.1]-nonane | 2 | 0.013 |
| 3-(3,4-Dichlorophenyl)-9-methyl-3,9-diazabicyclo-[4.2.1]-nonane | A1 | 0.032 |
| 3-(6-Nitro-2-quinolinyl)-9-methyl-3,9-diazabicyclo-[4.2.1]-nonane | C3 | 0.0037 |
| 3-(2-Naphthalyl)-9-methyl-3,9-diazabicyclo-[4.2.1]-nonane | 1 | 0.04 |
| 3-(3-Quinolinyl)-9-H-3,9-diazabicyclo-[4.2.1]-nonane | B5 | 0.049 |

Example 3

Biological Activity

The affinity of compounds of the invention for nicotinic ACh receptors have been investigated in three test for in vitro inhibition of $^3$H-cytisine binding and $^3$H-α-bungarotoxin binding and as described below.

In Vitro Inhibition of $^3$H-Cytisine Binding

Molecular biology studies have elucidated that there are at least ten nicotinic receptor genes in the brain. The predominant subtype with high affinity for nicotine is comprised of $α_4$ and $β_2$ subunits. nAChRs of the latter type can selectively be labelled by the nicotine agonist $^3$H-cytisine.

Preparations are performed at 0–4° C.

Cerebral corticies from male Wistar rats (150–250 g) are homogenized for 20 sec in 15 ml Tris, HCl (50 mM, pH 7.4) containing 120 mM NaCl, 5 mM KCl, 1 mM MgCl$_2$ and 2.5 mM CaCl$_2$ using an Ultra-Turrax homogenizer. The homogenate is centrifuged at 27,000×g for 10 min. The supernatant is discarded and the pellet is resuspended in fresh buffer and centrifuged a second time. The final pellet is resuspended in fresh buffer (35 ml per g of original tissue) and used for binding assays.

Aliquots of 500 μl homogenate are added to 25 μl of test solution and 25 μl of $^3$H-cytisine (1 nM, final concentration), mixed and incubated for 90 min at 2° C. Non-specific binding is determined using (−)-nicotine (100 μM, final concentration). After incubation the samples are added 5 ml of ice-cold buffer and poured directly onto Whatman GF/C glass fibre filters under suction and immediately washed with 2×5 ml ice-cold buffer. The amount of radioactivity on the filters is determined by conventional liquid scintillation counting. Specific binding is total binding minus non-specific binding.

The test value is given as an $IC_{50}$ (the concentration (μM) of the test substance which inhibits the specific binding of $^3$H-cytisine by 50%).

The $IC_{50}$ value is determined from the inhibition curve. If a full curve is not available a 25–75% inhibition of specific binding must be obtained, before calculation of an $IC_{50}$.

$$IC_{50} = \text{(applied test substance concentration, μM)} \times \frac{1}{\left(\frac{C_0}{C_x} - 1\right)}$$

where $C_0$ is specific binding in control assays and $C_x$ is the specific binding in the test assay (the calculations assume normal mass-action kinetics).

The results are presented in Table 2 below.

In Vitro Inhibition of $^3$H-α-Bungarotoxin Binding

α-Bungarotoxin is a peptide isolated from the venom of the Elapidae snake *Bungarus multicinctus* [Mebs et al.; *Biochem. Biophys. Res. Commun.* 1971 44 (3) 711] and has high affinity for neuronal and neuromuscular nicotinic receptors, where it acts as a potent antagonist. $^3$H-α-Bungarotoxin binds to a single site in rat brain with an unique distribution pattern in rat brain [Clarke et al.; *J. Neurosci.* 1985 5 1307–1315].

$^3$H-α-Bungarotoxin labels nAChR formed by the $α_7$ subunit isoform found in brain and the $α_1$ isoform in the neuromuscular junction [Changeaux; *Fidia Res. Found. Neurosci. Found. Lect.* 1990 4 21–168]. Functionally, the $α_7$ homo-oligomer expressed in oocytes has a calcium permeability greater than neuromuscular receptors and, in some instances greater than NMDA channels [Seguela et al.; *J. Neurosci.* 1993 13 596–604].

Preparations are performed at 0–4° C.

Cerebral cortices from male Wistar rats (150–250 g) are homogenized for 10 sec in 15 ml 20 mM Hepes buffer containing 118 mM NaCl, 4.8 mM KCl, 1.2 mM MgSO$_4$ and 2.5 mM CaCl$_2$ (pH 7.5) using an Ultra-Turrax homogenizer. The tissue suspension is centrifuged at 27,000×g for 10 min. The supernatant is discarded and the pellet is washed twice by centrifugation at 27,000×g for 10 min in 20 ml fresh buffer, and the final pellet is resuspended in fresh buffer containing 0.01% BSA (35 ml per g of original tissue) and used for binding assays.

Aliquots of 500 μl homogenate are added to 25 μl of test solution and 25 μl of $^3$H-α-bungarotoxin (2 nM, final concentration), mixed and incubated for 2 h at 37° C. Non-specific binding is determined using (−)-nicotine (1 mM, final concentration). After incubation the samples are added 5 ml of ice-cold Hepes buffer containing 0.05% PEI and poured directly onto Whatman GF/C glass fibre filters (presoaked in 0.1% PEI for at least 6 h) under suction and immediately washed with 2×5 ml ice-cold buffer. The amount of radioactivity on the filters is determined by conventional liquid scintillation counting. Specific binding is total binding minus non-specific binding.

The test value is given as an IC$_{50}$ (the concentration (μM) of the test substance which inhibits the specific binding of $^3$H-α-bungarotoxin by 50%).

The IC$_{50}$ value is determined from the inhibition curve. If a full curve is not available a 25–75% inhibition of specific binding must be obtained, before calculation of an IC$_{50}$.

$$IC_{50} = \text{(applied test substance concentration, μM)} \times \frac{1}{\left(\frac{C_0}{C_x} - 1\right)}$$

where $C_0$ is specific binding in control assays and $C_x$ is the specific binding in the test assay (the calculations assume normal mass-action kinetics).

The results are presented in Table 2 below.

TABLE 2

| Compound | Compound No. | $^3$H-cytisine binding IC$_{50}$ (μM) | $^3$H-α-bungarotoxin binding IC$_{50}$ (μM) |
|---|---|---|---|
| O,O'-bis-[5-(9-Methyl-3,9-diazabicyclo-[4.2.1]-nonan-3-yl)-3-pyridyl]-ethyleneglycol | B7 | 0.013 | >10 |
| 3-(6-Phenyl-3-pyridazinyl)-9-methyl-3,9-diazabicyclo-[4.2.1]-nonane | C2 | >10 | 0.41 |
| 3-[6-(2-Toluyl)-3-pyridyl]-9-methyl-3,9-diazabicyclo-[4.2.1]-nonane | F1 | 0.099 | 5.5 |
| 3-[6-(3-Thienyl)-3-pyridyl]-9-methyl-3,9-diazabicyclo-[4.2.1]-nonane | F5 | 1.5 | 0.28 |
| 3-Methyl-9-(6-phenyl-3-pyridazinyl)-3,9-diazabicyclo-[4.2.1]-nonane | F10 | 27 | 0.8 |

The invention claimed is:

1. A 3,9-diazabicyclo-[4.2.1]-nonane compound of Formula I

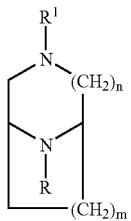

(I)

any of its enantiomers or any mixture thereof, an N oxide thereof, or a pharmaceutically acceptable salt thereof, in a labelled or un-labelled form,
wherein,
n is 2; and
m is 1; and
one of R and R$^1$ represents hydrogen, alkyl, cycloalkyl, cycloalkylalkyl, alkenyl, alkynyl, a mono- or polycyclic aryl or aralkyl group; and
the other of R and R$^1$ represents a phenyl or naphthyl group,
which aryl group may be substituted one or more times with alkyl, cycloalkyl, cycloalkylalkyl, alkoxy, hydroxyalkoxy, alkoxycycloalkyl, cycloalkoxy, cycloalkoxyalkoxy, alkenyl, alkenoxy, alkoxyalkenyl, alkynyl, alkynoxy, alkoxyalkynyl, alkylthio, alkenylthio, alkynylthio, alkylseleno, alkenylseleno, alkynylseleno, methylenedioxy, trifluoromethanesulfonyloxy, halogen, -OH, trihalogenmethyl, trihalogenmethoxy, -CN, amino, nitro, oxime, alkyloxime, or a group of the formula —COOR$^3$, —CONR$^2$R$^3$, —NH—CO$_2$R$^2$, —NHCO—R$^2$, —OCO—NR$^2$R$^3$; in which formulae R$^2$ and R$^3$ independently of each another represents hydrogen or alkyl; or
the other of R and R$^1$ represents a bicyclic or tricyclic heterocyclic group containing one or more heteroatoms selected from the group consisting of nitrogen, oxygen and sulphur,
which bi- or tricyclic heterocyclic group may be substituted one or more times with alkyl; cycloalkyl; cycloalkylalkyl; alkenyl; alkynyl; alkoxy; alkoxyalkoxy; cycloalkoxy; alkenoxy; alkynoxy; methylenedioxy; halogen; —OH; trihalogenmethyl, trihalogenmethoxy; —CN; amino; nitro; oxime; or alkyloxime.

2. The 3,9-diazabicyclo-[4.2.1]-nonane compound of claim 1, wherein
one of R and R$^1$ represents hydrogen or alkyl, and
the other of R and R$^1$ represents phenyl or naphthyl, which aryl group may be substituted once or twice with halogen, alkyl, alkoxy, trihalogenmethyl, trihalogenmethoxy, amino, —NHCO—alkyl, nitro, phenyl or pyrrolidinyl.

3. The 3,9-diazabicyclo-[4.2.1]-nonane compound of claim 2, wherein
one of R or R$^1$ represents hydrogen or methyl, and
the other of R or R$^1$ represents a phenyl group or a naphthyl group, which aryl groups may be substituted once or twice with chloro, bromo, fluoro, methoxy, trifluoromethyl, trifluoromethoxy, amino, —NHCO—CH$_3$, nitro, phenyl or pyrrolidinyl.

4. The 3,9-diazabicyclo-[4.2.1]-nonane compound of claim 3, which is
(±) 3-(2-Naphthalyl)-9-methyl-3,9-diazabicyclo-[4.2.1]-nonane;
(±) 3-(3,4-Dichlorophenyl)-9-methyl-3,9-diazabicyclo-[4.2.1]-nonane;
(±) 3-(4-Fluorophenyl)-9-methyl-3,9-diazabicyclo-[4.2.1]-nonane;
(±) 3-(3-Fluorophenyl)-9-methyl-3,9-diazabicyclo-[4.2.1]-nonane;
(±) 3-(4-Trifluoromethoxyphenyl)-9-methyl-3,9-diazabicyclo-[4.2.1]-nonane;
(±) 3-(3-Trifluoromethoxyphenyl)-9-methyl-3,9-diazabicyclo-[4.2.1]-nonane;
(±) 3-(Phenyl)-9-methyl-3,9-diazabicyclo-[4.2.1]-nonane;
(±) 3-(3-Chlorophenyl)-9-methyl-3,9-diazabicyclo-[4.2.1]-nonane;
(±) 3-(3-Bromophenyl)-9-methyl-3,9-diazabicyclo-[4.2.1]-nonane
(±) 3-(4-Biphenylyl)-9-methyl-3,9-diazabicyclo-[4.2.1]-nonane
(±) 3-(3,4-Dichlorophenyl)-9-H-3,9-diazabicyclo-[4.2.1-]-nonane;
(±) 3-Phenyl-9-H-3,9-diazabicyclo-[4.2.1]-nonane;
(±) 3-(3-Chlorophenyl)-9-H-3,9-diazabicyclo-[4.2.1]-nonane;
(±) 3-(4-Biphenylyl)-9-H-3,9-diazabicyclo-[4.2.1]-nonane;
(±) 3-(4-Nitrophenyl)-9-methyl-3,9-diazabicyclo-[4.2.1]-nonane;
(±) 3-(4-Trifluoromethylphenyl)-9-methyl-3,9-diazabicyclo-[4.2.1]-nonane;

(±) 3-(4-Aminophenyl)-9-methyl-3,9-diazabicyclo-[4.2.1]-nonane;

(±) 3-(4-Acetylaminophenyl)-9-methyl-3,9-diazabicyclo-[4.2.1]-nonane;

(±) 3-[4-(N-Pyrrolidinylphenyl)]-9-methyl-3,9-diazabicyclo-[4.2.1]-nonane;

any of its enantiomers or any mixture thereof, an N oxide thereof, or a pharmaceutically acceptable salt thereof, in a labelled or un-labelled form.

5. The 3,9-diazabicyclo-[4.2.1]-nonane compound of claim 1, wherein one of R and $R^1$ represents hydrogen or alkyl, and the other of R and $R^1$ represents a bi- or tricyclic 5- to 6-membered heterocyclic group containing one or more heteroatoms selected from the group consisting of nitrogen, oxygen and sulphur, which heterocyclic group may be substituted once or twice with halogen, alkyl, alkoxy, trihalogenmethyl, trihalogenmethoxy, nitro or phenyl.

6. The 3,9-diazabicyclo-[4.2.1]-nonane compound of claim 5, wherein one of R and $R^1$ represents hydrogen or alkyl, and the other of R and $R^1$ represents a quinolinyl group, a naphtyridinyl group, an N-methyl-carbazolyl group, a dibenzothiophenyl group, or a dibenzofuryl group, which heterocyclic groups may be substituted once or twice with halogen, alkyl, alkoxy, trihalogenmethyl, trihalogenmethoxy, nitro or phenyl.

7. The 3,9-diazabicyclo-[4.2.1]-nonane compound of claim 6, which is (±) 3-(2-Quinolinyl)-9-methyl-3,9-diazabicyclo-[4.2.1]-nonane;

(±) 3-(6-Quinolinyl)-9-methyl-3,9-diazabicyclo-[4.2.1]-nonane;

(±) 3-(3-Quinolinyl)-9-methyl-3,9-diazabicyclo-[4.2.1]-nonane;

(±) 3-(3-Quinolinyl)-9-H-3,9-diazabicyclo-[4.2.1]-nonane;

(±) 3-(4-Methyl-2-quinolinyl)-9-methyl-3,9-diazabicyclo-[4.2.1]-nonane;

(±) 3-(6-Nitro-2-quinolinyl)-9-methyl-3,9-diazabicyclo-[4.2.1]-nonane;

(±) 3-(6-Nitro-2-quinolinyl)-9-H-3,9-diazabicyclo-[4.2.1]-nonane;

(±) 3-[2-(1,8-Naphtyridinyl)]-9-H-3,9-diazabicyclo-[4.2.1]-nonane;

(±) 3-[2-(1,8-Naphtyridinyl)]-9-methyl-3,9-diazabicyclo-[4.2.1]-nonane;

(±) 3-[2-(1,5-Naphtyridinyl)]-9-H-3,9-diazabicyclo-[4.2.1]-nonane;

(±) 3-[2-(1,5-Naphtyridinyl)]-9-methyl-3,9-diazabicyclo-[4.2.1]-nonane;

(±) 3-[2-(N-Methyl-carbazolyl)]-9-H-3,9-diazabicyclo-[4.2.1]-nonane;

(±) 3-[2-(N-Methyl-carbazolyl)]-9-methyl-3,9-diazabicyclo-[4.2.1]-nonane;

(±) 3-(2-Dibenzothiophenyl)-9-H-3,9-diazabicyclo-[4.2.1]-nonane;

(±) 3-(2-Dibenzothiophenyl)-9-methyl-3,9-diazabicyclo-[4.2.1]-nonane;

(±) 3-(2-Dibenzofuryl)-9-H-3,9-diazabicyclo-[4.2.1]-nonane; or (±) 3-(2-Dibenzofuryl)-9-methyl-3,9-diazabicyclo-[4.2.1]-nonane;

any of its enantiomers or any mixture thereof, an N oxide thereof, or a pharmaceutically acceptable salt thereof, in a labelled or un-labelled form.

8. A pharmaceutical composition comprising a therapeutically effective amount of a 3,9-diazabicyclo-[4.2.1]-nonane compound of claim 1, or a pharmaceutically-acceptable addition salt thereof, together with at least one pharmaceutically-acceptable carrier or diluent.

9. A method of treatment, prevention or alleviation of a disease or a disorder or a condition of a living animal body, wherein the disease, disorder or condition is associated with withdrawal symptoms caused by termination of use of a nicotine containing product, which method comprises the step of administering to such a living animal body in need thereof a therapeutically effective amount of a 3,9-diazabicyclo-[4.2.1]-nonane compound of claim 1.

10. The method of claim 9, wherein the nicotine-containing product is tobacco.

* * * * *